United States Patent
Ebi et al.

(10) Patent No.: US 9,945,783 B2
(45) Date of Patent: Apr. 17, 2018

(54) CERVICAL CANCER INFORMATION PROVIDING METHOD AND DEVICE

(71) Applicant: Sysmex Corporation, Kobe-shi (JP)

(72) Inventors: Ryuichiro Ebi, Kobe (JP); Koki Tajima, Kobe (JP); Shigeki Abe, Kobe (JP)

(73) Assignee: SYSMEX CORPORATION, Chuo-Ku, Kobe-Shi, Hyogo (JP)

( * ) Notice: Subject to any disclaimer, the term of this patent is extended or adjusted under 35 U.S.C. 154(b) by 433 days.

(21) Appl. No.: 13/845,674

(22) Filed: Mar. 18, 2013

(65) Prior Publication Data

US 2013/0280729 A1 Oct. 24, 2013

(30) Foreign Application Priority Data

Mar. 30, 2012 (JP) .................. 2012-083199

(51) Int. Cl.
  *G01N 21/64* (2006.01)
  *G01N 15/14* (2006.01)

(52) U.S. Cl.
  CPC ..... *G01N 21/6486* (2013.01); *G01N 15/1475* (2013.01); *G01N 2015/1486* (2013.01); *G01N 2015/1488* (2013.01)

(58) Field of Classification Search
  None
  See application file for complete search history.

(56) References Cited

U.S. PATENT DOCUMENTS

2008/0108103 A1  5/2008  Ishisaka et al.

FOREIGN PATENT DOCUMENTS

| JP | 2004-286666 A | 10/2004 |
|----|---------------|---------|
| JP | 2011-095182 A | 5/2011 |
| JP | 2011-133460 A | 7/2011 |
| WO | WO 2006/103920 A1 | 10/2006 |
| WO | WO 2009/057525 A1 | 5/2009 |
| WO | WO 2011/099565 A1 | 8/2011 |

OTHER PUBLICATIONS

Park, "Large liver cell dysplasia: a controversial entity," Journal of hepatology, vol. 45, p. 734-743, 2006.*
Watanabe, "Morphologic studies of the liver cell dysplasia," Cancer, vol. 51, p. 2197-2205, 1983.*
El-Sayed, "DNA ploidy and liver cell dysplasia in liver biopsies from patients with liver cirrhosis," Canadian journal of gastroenterology, vol. 18, p. 87-91, 2004.*
Gong, "Simultaneous analysis of cell cycle kinetics at two different DNA ploidy levels based on DNA content and cyclin B measurements," Cancer research, vol. 53, p. 5096-5099, 1993.*
Vermes, "Flow cytometry of apoptotic cell death," Journal of immunological methods, vol. 243(1), p. 167-190, 2000.*

* cited by examiner

*Primary Examiner* — G. Steven Vanni
(74) *Attorney, Agent, or Firm* — Brinks Gilson & Lione

(57) ABSTRACT

Provided is a canceration information providing method capable of presenting the information related to canceration of the cells with high reliability. A cell in which the amount of DNA is greater than or equal to the amount of DNA of the normal cell in the S period is extracted from a cell group of V11≤N/C ratio≤V12 (first counting step). If the number of cells obtained in the first counting step is greater than or equal to the threshold value S1 (S107: YES), "Cancer" is set to a flag 1. A cell in which the amount of DNA is 2C is extracted from a cell group of V13≤N/C ratio≤V11 (second counting step). A ratio of the number of cells obtained in the second counting step and number of cells obtained in the first counting step is calculated, and "Cancer" is set to a flag 2 if the ratio is greater than or equal to a threshold value S2 (S111: YES). If one of the flags 1, 2 is "Cancer" (S113: YES), the display of retest necessary is performed.

13 Claims, 19 Drawing Sheets

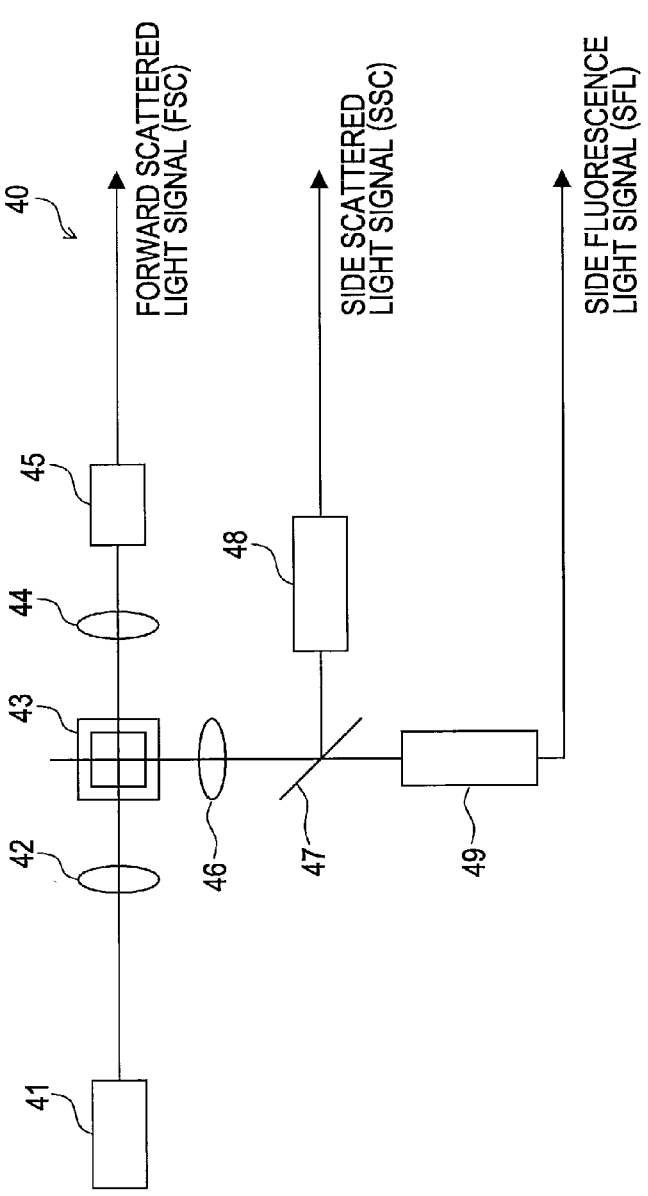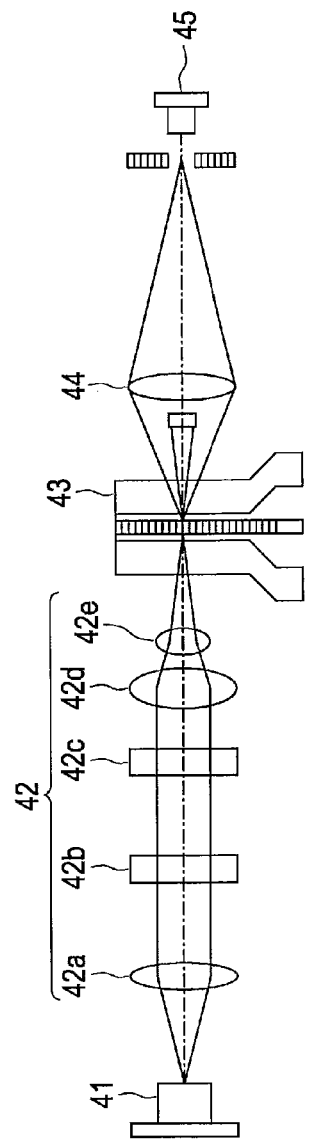
FIG. 3A
FIG. 3B

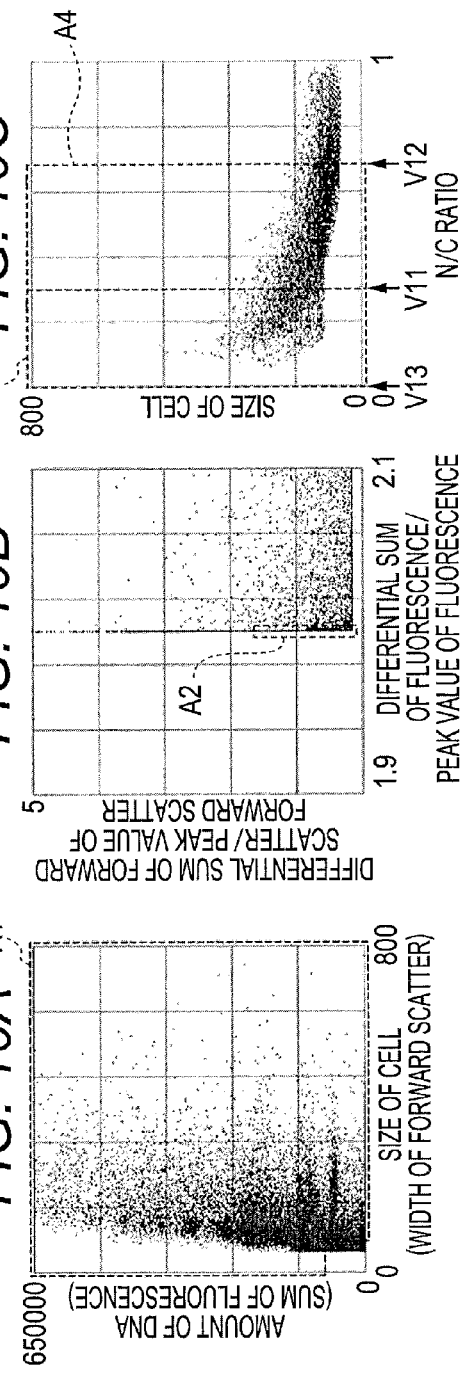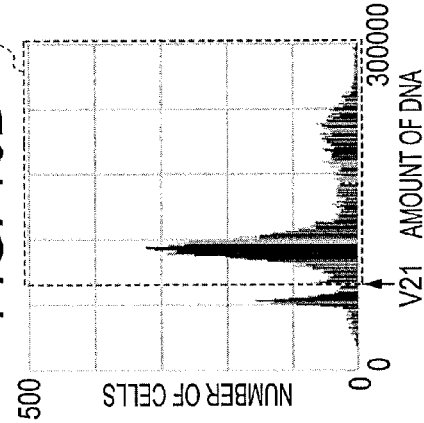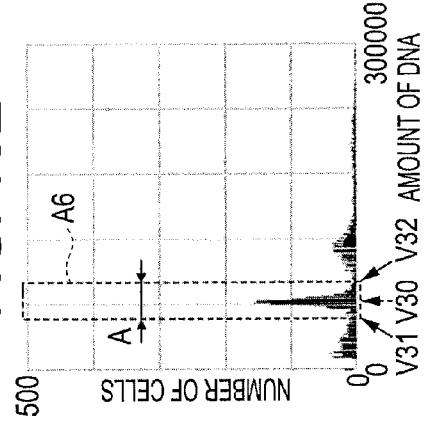

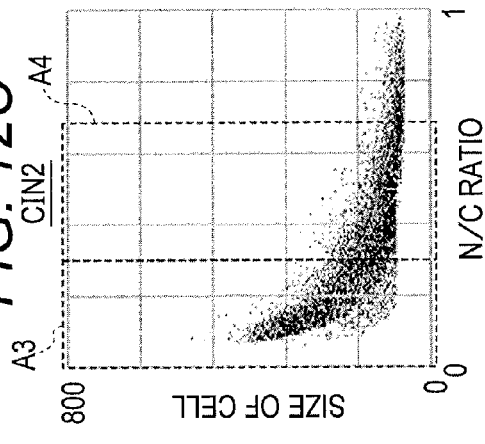
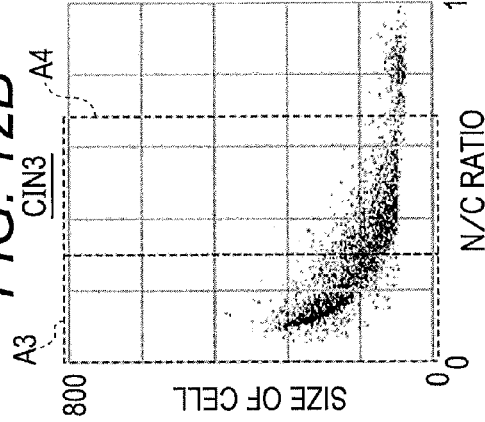
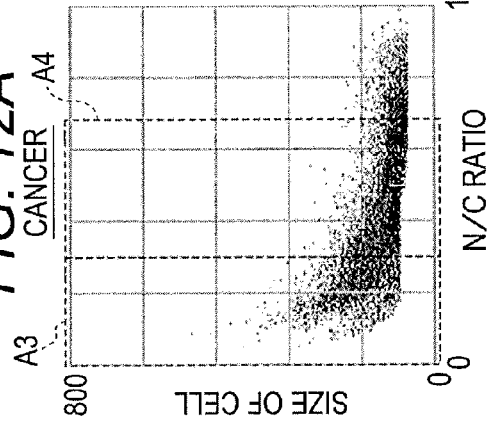
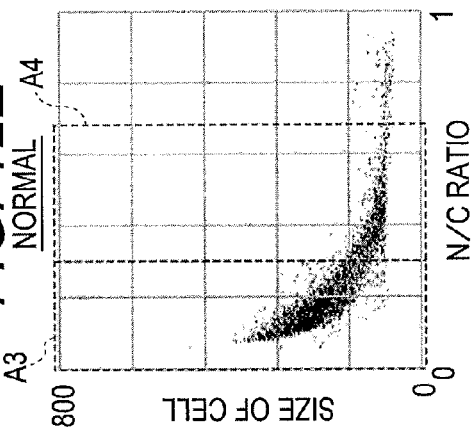
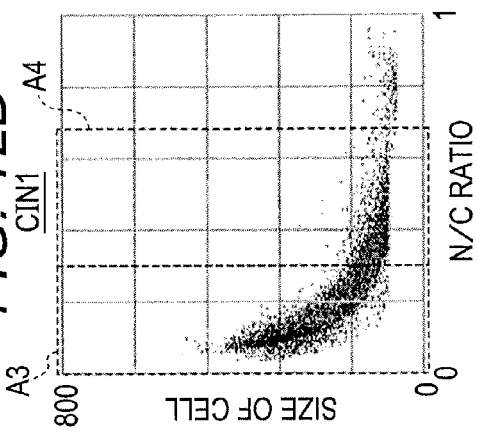

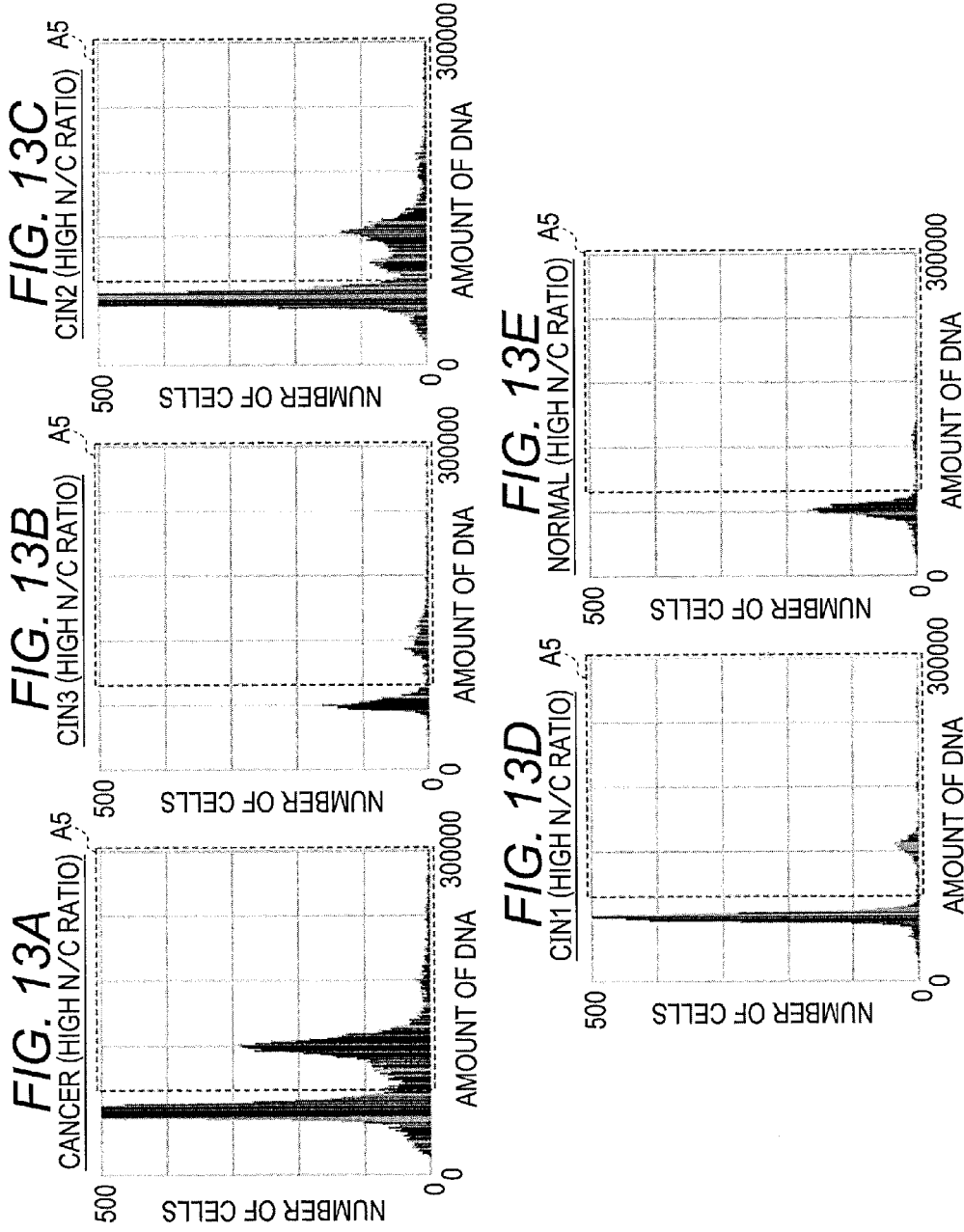

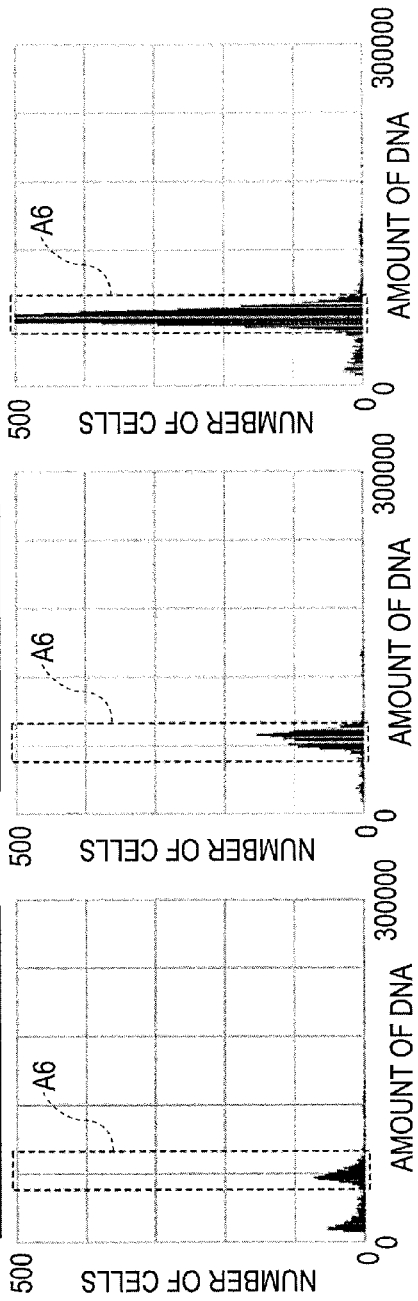

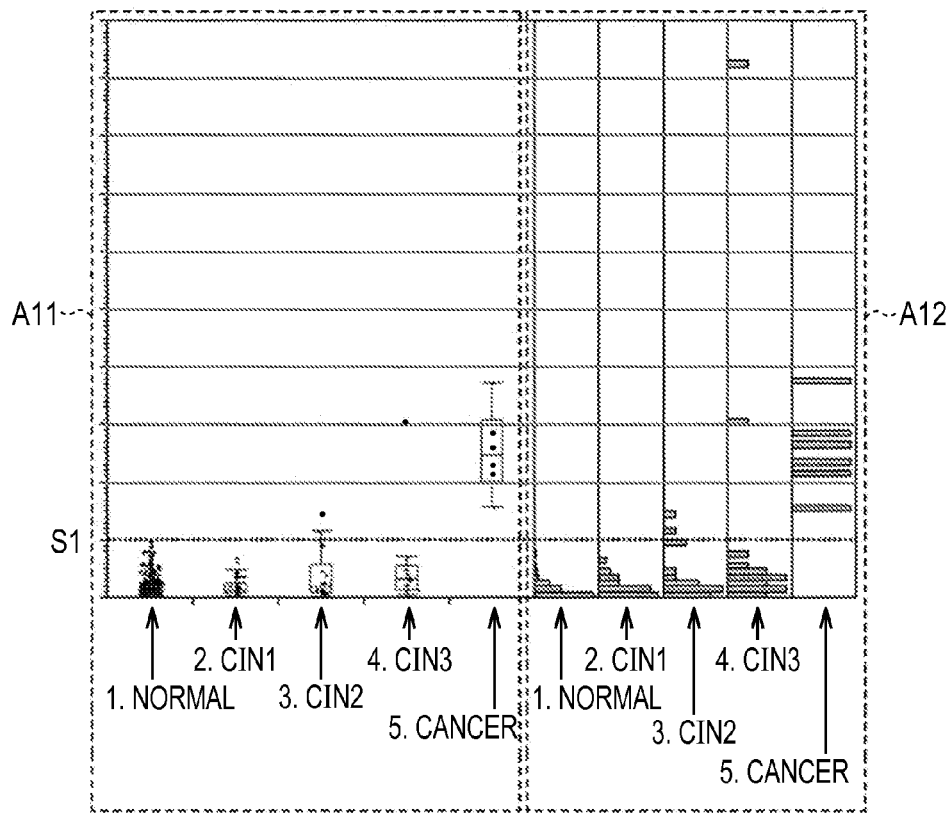

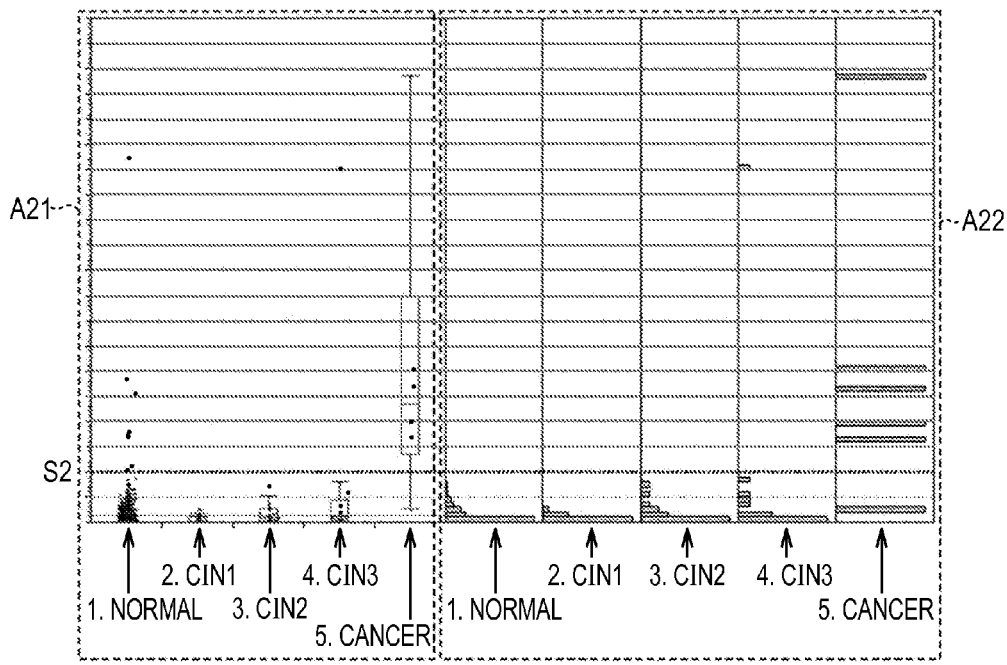

PATTERN 1

PATTERN 2

PATTERN 3

PATTERN 4

CERVICAL CANCER INFORMATION PROVIDING METHOD AND DEVICE

RELATED APPLICATIONS

This application claims priority under 35 U.S.C. §119 to Japanese Patent Application No. 2012-083199 filed on Mar. 30, 2012, the entire content of which is hereby incorporated by reference.

BACKGROUND OF THE INVENTION

1. Field of the Invention

The present invention relates to a canceration information providing method and a canceration information providing device for analyzing cells and providing information related to canceration of the cells.

2. Description of the Related Art

An analyzer for automatically analyzing the cells of a subject and providing information related to the canceration of the cells is known (see e.g., U.S. Patent Application publication No. 2008/108103). U.S. Patent Application publication No. 2008/108103 discloses a device that flows a measurement specimen including cells collected from a subject to a flow cell, irradiates the measurement specimen flowing through the flow cell with light to acquire a scattered light signal for the individual cell, extracts a characteristic parameter by analyzing the waveform of each scattered light signal, and discriminates cancer/atypical cell from a plurality of cells using the characteristic parameter.

For example, in the tissue diagnosis of the uterine cervix, the process from the normal state to cancer has a plurality of stages, "Normal", "CIN1", "CIN2", "CIN3", and "Cancer" in order from the normal state. "CIN1" is a state in which the atypical cells are growing in one third from a basal layer to a surface layer, and is a state in which the possibility of regressing spontaneously is high. Thus, treatment is determined as unnecessary in "CIN1". "CIN2" is a state in which the atypical cells are growing in two thirds from the basal layer to the surface layer. "CIN3" is a state in which the atypical cells are growing substantially entirely from the basal layer to the surface layer. Treatment is sometimes determined as necessary in "CIN2" and "CIN3". If the state of "CIN3" further advances, this results in "Cancer". When reaching "Cancer", immediate treatment is particularly necessary, and it is very important that this state is reliably detected.

The analyzer described in U.S. Patent Application publication No. 2008/108103 has a problem in that "CIN1" in which treatment is unnecessary is determined as "Cancer", or so-called false alarm increases when trying to reliably detect "Cancer" since the atypical cells also exist in the "CIN1". When attempting to reduce such false alarm, it may become difficult to reliably detect "Cancer".

SUMMARY OF THE INVENTION

The scope of the present invention is defined solely by the appended claims, and is not affected to any degree by the statements within this summary.

In light of the foregoing, it is an object of the present invention to provide a canceration information providing method and a canceration information providing device capable of accurately grasping the advancement of the tissue to the cancer level, and presenting the information related to the canceration of the cells at high reliability based thereon.

A first aspect of the present invention is a canceration information providing method for providing information related to canceration of cells, the method comprising: acquiring measurement data including first data related to size of a cell nucleus, second data related to size of a cell, and third data related to amount of DNA of the cell for each cell to be analyzed contained in a measurement specimen, which includes the cells collected from epidermal tissue; acquiring a number of first cells in which a ratio of the size of the cell nucleus with respect to the size of the cell is smaller than a predetermined threshold value and having an amount of DNA of a normal cell in which a cell cycle is in a G0 period or a G1 period out of the cells to be analyzed based on the first data, the second data, and the third data; acquiring a number of second cells having an amount of DNA exceeding the amount of DNA of the normal cell in which the cell cycle is in G0 period or G1 period out of the cells to be analyzed based on the third data; calculating a ratio of the acquired number of first cells and the number of second cells; and outputting information related to the canceration of the cells based on the obtained ratio.

A second aspect of the present invention is a canceration information providing device for providing information relating to canceration of cells, the canceration information providing device comprising a controller configured for performing operations comprising: acquiring measurement data including first data related to size of a cell nucleus, second data related to size of a cell, and third data related to amount of DNA of the cell for each cell to be analyzed contained in a measurement specimen, which includes the cell collected from epidermal tissue; acquiring a first number of cells in which a ratio of the size of the cell nucleus with respect to the size of the cell is smaller than a predetermined threshold value and having an amount of DNA of a normal cell in which a cell cycle is in a G0 period or a G1 period out of the cells to be analyzed based on the first data, the second data, and the third data; acquiring a second number of cells having an amount of DNA exceeding the amount of DNA of the normal cell in which the cell cycle is in G0 period or G1 period out of the cells to be analyzed based on the third data; calculating a ratio of the acquired first number of cells and the second number of cells; and outputting information relating to the canceration of the cells based on the obtained ratio.

A third aspect of the present invention is a non-transitory storage medium which stores programs executable comprehensively by at least one processor, the programs causing the at least one processor to perform a method for providing information related to cancer cells, the method comprising: acquiring measurement data including first data related to size of a cell nucleus, second data related to size of a cell, and third data related to amount of DNA of the cell for each cell to be analyzed contained in a measurement specimen, which includes the cells collected from epidermal tissue; acquiring a first number of cells in which a ratio of the size of the cell nucleus with respect to the size of the cell is smaller than a predetermined threshold value and having an amount of DNA of a normal cell in which a cell cycle is in a G0 period or a G1 period out of the cells to be analyzed based on the first data, the second data, and the third data; acquiring a second number of cells having an amount of DNA exceeding the amount of DNA of the normal cell in which the cell cycle is in G0 period or G1 period out of the cells to be analyzed based on the third data; calculating a ratio of the acquired first number of cells and the second number of cells; and outputting information relating to the canceration of the cells based on the obtained ratio.

According to the present invention, a canceration information providing method and a canceration information providing device capable of accurately grasping the advancement of the tissue to the cancer level, and presenting the information related to the canceration of the tissue at high reliability based thereon can be provided.

The effects and significance of the present invention should become more apparent from the description of the embodiment described below. It should be recognized that the embodiment described below is merely one illustration in implementing the present invention, and the present invention is not to be limited by the embodiment described below.

BRIEF DESCRIPTION OF THE DRAWINGS

FIGS. 3A and 3B are views showing a configuration of a flow cytometer according to the present embodiment;

FIGS. 10A-10E are views showing scattergrams and histograms generated by the analysis processing according to the present embodiment;

FIGS. 12A-12E are views showing scattergrams of samples in which the degree of advancement of the cancer differs according to the present embodiment;

FIGS. 13A-13E are histograms created by extracting the cell group contained in the region of high N/C ratio for samples in which the degree of advancement of the cancer differs according to the present embodiment;

FIGS. 14A-14E are histograms created by extracting the cell group contained in the region of low N/C ratio for samples in which the degree of advancement of the cancer differs according to the present embodiment;

FIGS. 15A-15C are views describing a relationship of the determination result of the tissue diagnosis and the determination result by the determination 1 according to the present embodiment;

FIGS. 16A-16E are views describing a relationship of the determination result of the tissue diagnosis and the determination result according to the determination 2, and a view describing a relationship of the determination result of the tissue diagnosis and the final determination result according to the present embodiment;

DETAILED DESCRIPTION OF THE PREFERRED EMBODIMENTS

The preferred embodiments of the present invention will be described hereinafter with reference to the drawings.

A canceration information providing device 1 according to the present embodiment will be hereinafter described with reference to the drawings.

The canceration information providing device 1 flows a measurement specimen, which includes a cell (biological specimen) collected from a patient (subject), to a flow cell, and irradiates the measurement specimen flowing through the flow cell with a laser light. Light (forward scattered light, side scattered light, side fluorescence) from the measurement specimen is then detected and the obtained light signals are analyzed to determine if the cell contains cancerous cells or cells in the process of becoming cancerous (hereinafter collectively referred to as "cancerous cell"). Specifically, the canceration information providing device 1 is used when screening a uterine cervical cancer using epidermal cells of the uterine cervix collected from the patient.

Figure 1:
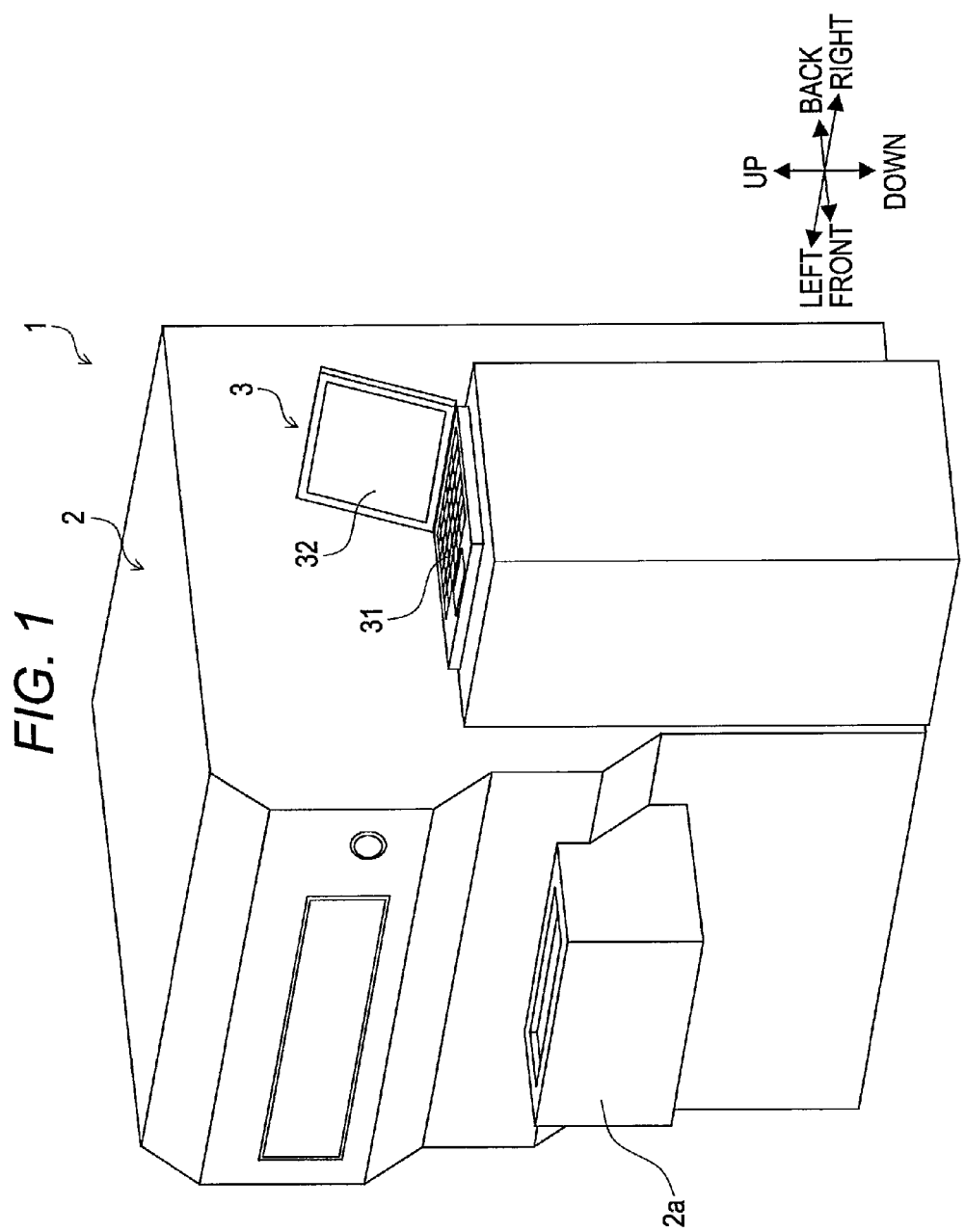
FIG. 1 is a perspective view schematically showing a configuration of an outer appearance of a canceration information providing device according to the present embodiment.

FIG. 1 is a perspective view schematically showing a configuration of an outer appearance of the canceration information providing device 1.

The canceration information providing device 1 includes a measurement device 2 that performs measurement, and the like of a biological specimen collected from the patient, and a data processing device 3 that is connected to the measurement device 2 and that performs analysis, display (output), and the like of the measurement result. On a front surface of the measurement device 2 is installed a sample setting unit 2a for setting a plurality of specimen containers 4 (see FIG. 2) accommodating a mixed solution (specimen) of a preservation solution, in which methanol is the main component, and the biological specimen collected from the patient. The data processing device 3 includes an input unit 31 and a display unit 32.

Figure 2:
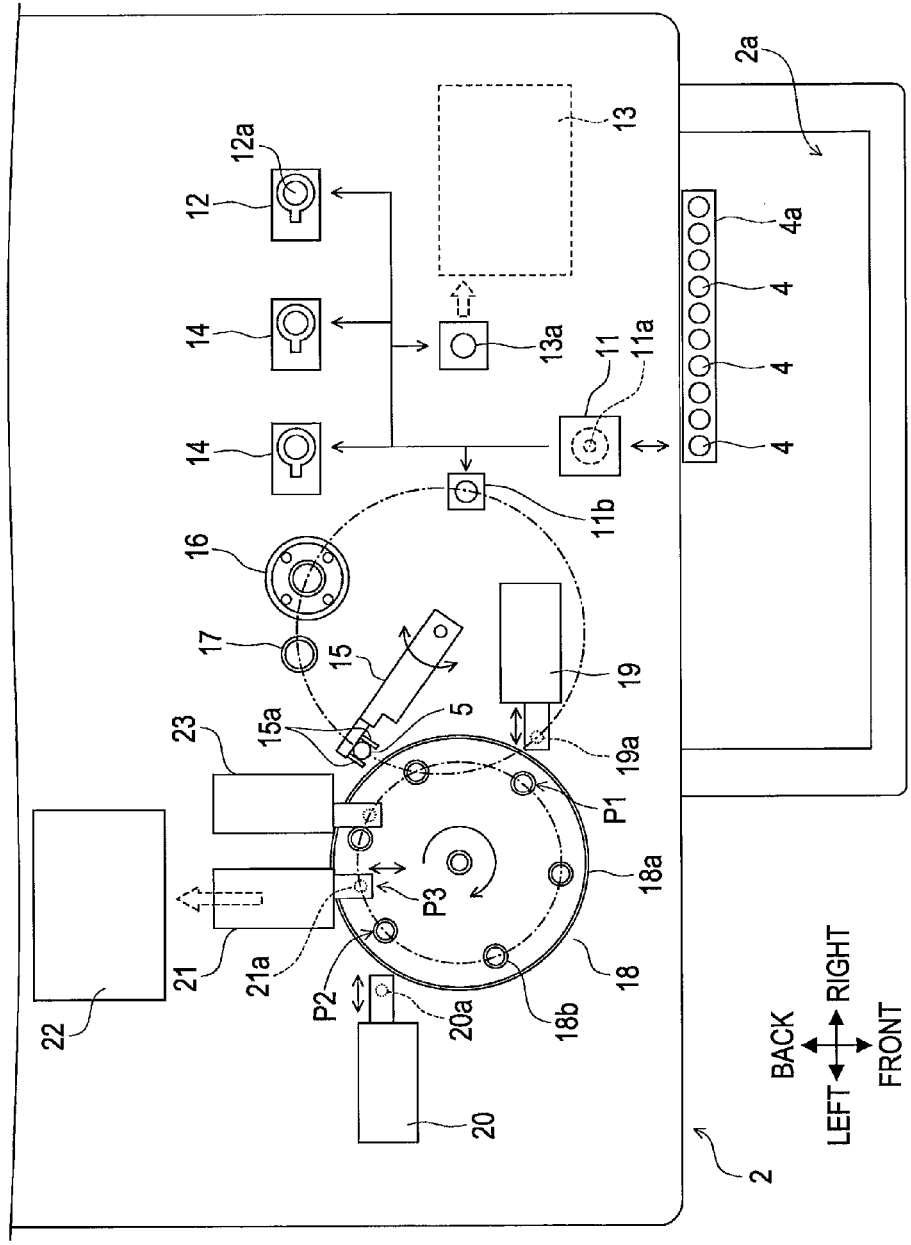
FIG. 2 is a plan view schematically showing a configuration of the inside of a measurement device according to the present embodiment.

FIG. 2 is a plan view schematically showing a configuration of the inside of the measurement device 2.

The sample setting unit 2a sequentially transports a rack 4a, in which a plurality of specimen containers 4 is set, to an aspirating position of the specimen by a sample pipette unit 11.

The sample pipette unit 11 transfers the specimen in the specimen container 4 to a first dispersion unit 12. The sample pipette unit 11 also transfers the specimen in the first dispersion unit 12 to a sub-detection unit 13 and a discriminating/replacing unit 14. The sample pipette unit 11 further supplies a concentrated solution concentrated in the discriminating/replacing unit 14 to a measurement specimen container 5. The sample pipette unit 11 is configured to be movable to an upper position of a specimen accommodating section 12a of the first dispersion unit 12, a specimen retrieving section 13a of the sub-detection unit 13, the discriminating/replacing unit 14, and the measurement specimen container 5 positioned in a specimen exchanging section 11b.

The sample pipette unit 11 includes a pipette 11a, which aspirates and discharges the specimen, and a sample quantity determining unit (not shown) (quantity determining cylinder, motor for driving a piston in the quantity determining cylinder, and the like). The sample pipette unit 11 determines the quantity of the specimen with the sample quantity determining unit to be able to supply a predetermined amount of specimen to each unit described above with the pipette 11a.

The first dispersion unit 12 executes first dispersion processing for dispersing aggregating cells contained in the specimen on the specimen. Specifically, the first dispersion processing is shear force application processing for applying shear force on the aggregating cells to disperse the aggregating cells. The first dispersion unit 12 includes a specimen accommodating section 12a capable of accommodating the specimen, and is configured to mechanically apply the shear force on the aggregating cells in the specimen supplied to the specimen accommodating section 12a.

The sub-detection unit 13 performs concentration measurement of the specimen before the actual measurement by a main detection unit 22. The sub-detection unit 13 adopts a flow cytometer 40 (see FIG. 3A) having a configuration substantially the same as the main detection unit 22, to be described later.

The discriminating/replacing unit 14 receives the specimen performed with the first dispersion processing of the first dispersion unit 12, and replaces the preservation solution, in which methanol is the main component, contained in the received specimen with a diluted solution. The discriminating/replacing unit 14 also discriminates the cell to be measured (epidermal cell, gland cell of the uterine cervix) contained in the specimen, and the cells (red blood cells, white blood cells, bacteria, etc.) as well as foreign substances other than the above cells. The discriminating/replacing unit 14 makes the specimen concentrated thus increasing the concentration of the cells to be measured contained in the specimen to obtain the number of cell measurements necessary for the measurement by the main detection unit 22. Two discriminating/replacing units 14 are arranged for efficiency of processing.

A container transfer unit 15 grips the measurement specimen container 5 set in a reaction unit 18 with a scissor-like grip section 15a, and transfers the measurement specimen container to the specimen exchanging section 11b, a second dispersion unit 16, a liquid removing unit 17, and the reaction unit 18. The container transfer unit 15 is configured to be able to move the grip section 15a along a predetermined circumferential path. The container transfer unit 15 is also configured to be able to move the grip section 15a in an up and down direction. The specimen exchanging section 11b, the second dispersion unit 16, the liquid removing unit 17, and the reaction unit 18 are arranged on the circumferential path. The measurement specimen container 5 set in the reaction unit 18 thus can be gripped by the grip section 15a of the container transfer unit 15 to be transferred to each unit on the circumferential path.

The second dispersion unit 16 executes second dispersion processing different from the first dispersion processing on the sample executed with the first dispersion processing by the first dispersion unit 12. Specifically, the second dispersion unit 16 is configured to apply an ultrasonic vibration on the sample executed with the first dispersion processing by the first dispersion unit 12 and concentrated (concentration of the cell to be measured is increased) in the discriminating/replacing unit 14. The aggregating cells remaining after the first dispersion processing are dispersed to single cells by the second dispersion unit 16.

The liquid removing unit 17 removes (drains) the liquid attached to the outer surface of the measurement specimen container 5 after the second dispersion processing by the second dispersion unit 16. The second dispersion processing is executed with the measurement specimen container 5 immersed in liquid. The liquid removing unit 17 is configured to remove water drops attached to the outer surface of the measurement specimen container 5 by supplying airflow to the outer surface of the measurement specimen container 5. The liquid is thus prevented from attaching to each unit when the measurement specimen container 5 is set in each unit such as the reaction unit 18.

The reaction unit 18 promotes the reaction between the specimen in the measurement specimen container 5 and the reagent added by a first reagent adding unit 19 and a second reagent adding unit 20. The reaction unit 18 includes a circular rotation table 18a configured to be rotatable by a drive unit (not shown). A plurality of holders 18b, to which the measurement specimen container 5 can be set, are arranged at the outer peripheral edge of the rotation table 18a. The measurement specimen container 5 is set in the holder 18b. The path of the holder 18b formed by the rotation of the rotation table 18a and the circumferential path of the grip section 15a of the container transfer unit 15 cross at a predetermined position, where the container transfer unit 15 can set the measurement specimen container 5 in the holder 18b at the crossed position. The reaction unit 18 also warms the measurement specimen container 5 set in the holder 18b to a predetermined temperature (about 37 degrees) to promote the reaction between the specimen and the reagent.

The first reagent adding unit 19 and the second reagent adding unit 20 supply reagent to the measurement specimen container 5 set in the holder 18b. The first reagent adding unit 19 and the second reagent adding unit 20 respectively includes a supply portion 19a, 20a that is installed at positions near the peripheral edge of the rotation table 18a, and can be moved to positions P1, P2 on the upper side of the measurement specimen container 5 set in the rotation table 18a. When the measurement specimen container 5 is transported to the position P1, P2 by the rotation table 18a, a predetermined amount of reagent is added into the measurement specimen container 5 from the supply portion 19a, 20a.

The reagent added by the first reagent adding unit 19 is RNase for performing an RNA removal processing on the cell. The reagent added by the second reagent adding unit 20 is stain fluid for performing a DNA staining processing on the cell. The RNA in the cell is disintegrated by the RNA removing process, so that only the DNA of the cell nucleus can be measured. The DNA staining processing is carried out with propidium iodide (PI), which is a fluorescence stain fluid containing pigment, where the nucleus in the cell can be selectively stained by the DNA staining processing. The fluorescence from the nucleus thus can be detected.

A specimen aspirating unit 21 aspirates the specimen (measurement specimen) in the measurement specimen container 5 set in the holder 18b and transfers the aspirated measurement specimen to the main detection unit 22. The specimen aspirating unit 21 includes a pipette 21a that is installed at a position near the peripheral edge of the rotation table 18a, and can be moved to a position P3 on the upper side of the measurement specimen container 5 set in the rotation table 18a. Thus, when the measurement specimen container 5 is transported to the position P3 by the rotation table 18a, the measurement specimen in the measurement specimen container 5 can be aspirated. The specimen aspirating unit 21 is also connected to the flow cell 43 (see FIG. 3A) of the main detection unit 22 through a flow path (not shown), and is configured to be able to supply the measurement specimen aspirated by the pipette 21a to the flow cell 43 of the main detection unit 22.

The main detection unit 22 includes the flow cytometer 40 for detecting the light (forward scattered light, side scattered light, side fluorescence) from the measurement specimen, and outputs the signal based on each light to the post-stage circuit. The flow cytometer 40 will be described later with reference to FIGS. 3A, 3B.

A container washing unit 23 washes the inside of the measurement specimen container 5 after the measurement specimen is supplied to the main detection unit 22 by the specimen aspirating unit 21. The container washing unit 23 discharges washing fluid into the measurement specimen container 5 held by the holder 18b of the rotation table 18a to wash the inside of the measurement specimen container 5. Thus, contamination with other specimens can be suppressed when the same measurement specimen container 5 is used in the subsequent measurement process.

FIG. 3A is a view showing a configuration of the flow cytometer 40 of the main detection unit 22.

The laser light emitted from a semiconductor laser 41 is collected at the measurement specimen flowing through the flow cell 43 by a lens system 42 including a plurality of lenses. As described above, the specimen aspirated by the pipette 21a of the specimen aspirating unit 21 is supplied to the flow cell 43.

As shown in FIG. 3B, the lens system 42 is configured by a collimator lens 42a, a cylinder lens system (plane-convex cylinder lens 42b and biconcave cylinder lens 42c), and a condenser lens system (condenser lens 42d and condenser lens 42e) in order from the semiconductor laser 41 (left side in FIGS. 3A and 3B).

A light collecting lens 44 collects the forward scattered light of the cell in the measurement specimen to a scattered light detector including a photodiode 45. A light collecting lens 46 for the side collects the side scattered light and the side fluorescence of the cell to be measured and the nucleus in the relevant cell, and guides the light to a dichoric mirror 47. The dichroic mirror 47 reflects the side scattered light toward a photomultiplier (photomultiplier tube) 48 and transmits the side fluorescence toward a photomultiplier (photomultiplier tube) 49. The side scattered light is thus collected at the photomultiplier 48, and the side fluorescence is collected at the photomultiplier 49. Such lights reflect the characteristics of the cell and the nucleus in the measurement specimen.

The photodiode 45 and the photomultipliers 48, 49 convert the received light signal to an electric signal, and outputs a forward scattered light signal (FSC), a side scattered light signal (SSC), and a side fluorescence signal (SFL), respectively. Such output signals are amplified by a pre-amplifier (not shown), and output to a signal processing unit 24 (see FIG. 4) of the measurement device 2.

Figure 4:
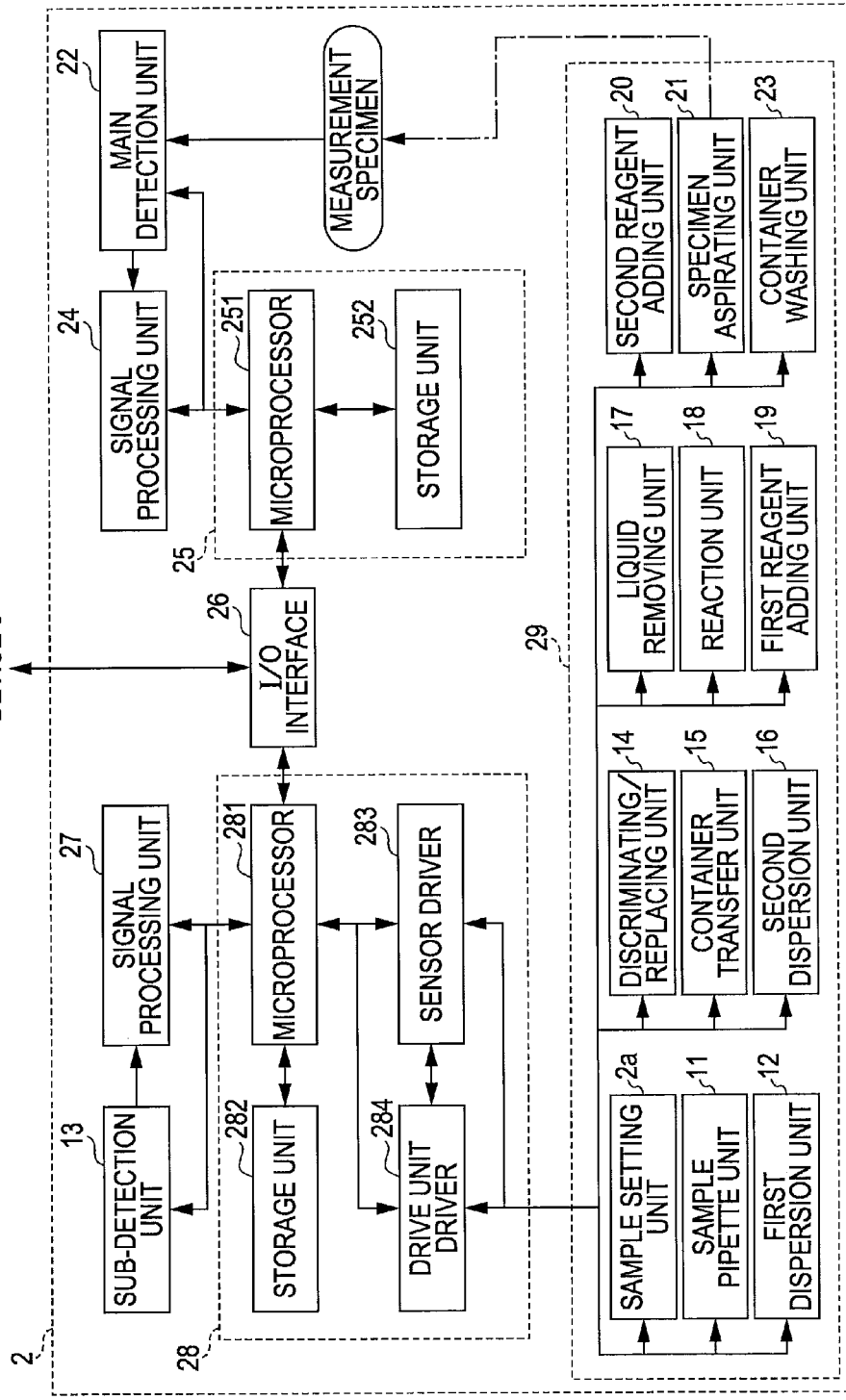
FIG. 4 is a view showing a configuration of a measurement device according to the present embodiment.

FIG. 4 is a view showing a configuration of the measurement device 2.

The measurement device 2 includes the main detection unit 22, the sub-detection unit 13 (shown in FIG. 2), and a preparation device unit 29 including each portion for automatically performing component adjustment on the specimen. The measurement device 2 also includes the signal processing unit 24, a measurement control unit 25, an I/O interface 26, a signal processing unit 27, and a preparation control unit 28.

As described above, the main detection unit 22 includes the flow cytometer 40 shown in FIG. 3A, and outputs the forward scattered light signal (FSC), the side scattered light signal (SSC), and the side fluorescence signal (SFL) from the measurement specimen. The signal processing unit 24 is configured by a signal processing circuit for performing necessary signal processing on the output signal from the main detection unit 22, and processes each signal FSC, SSC, SFL output from the main detection unit 22 and outputs to the measurement control unit 25.

The measurement control unit 25 includes a microprocessor 251 and a storage unit 252. The microprocessor 251 is connected to the data processing device 3 and a microprocessor 281 of the preparation control unit 28 through the I/O interface 26. The microprocessor 251 thus can transmit and receive various data with the data processing device 3 and the microprocessor 281 of the preparation control unit 28. The storage unit 252 is configured by a ROM for storing control programs and data such as the main detection unit 22, a RAM, or the like.

Each signal FSC, SSC, SFL processed by the signal processing unit 24 of the measurement device 2 is transmitted to the data processing device 3 through the I/O interface 26 by the microprocessor 251.

The sub-detection unit 13 adopts the flow cytometer 40 having a configuration substantially the same as the main detection unit 22, and thus the description of the configuration will be omitted. The sub-detection unit 13 performs concentration measurement of the specimen before the actual measurement by a main detection unit 22, and thus the sub-detection unit 13 merely needs to be able to output a signal for counting the number of cells. In other words, the sub-detection unit 13 merely needs to be able to acquire the forward scattered light signal (FSC). The signal processing unit 27 is configured by a processing circuit for performing necessary signal processing on the output signal from the sub-detection unit 13, and processes the forward scattered signal FSC output from the sub-detection unit 13 and outputs the same to the preparation control unit 28.

The preparation control unit 28 includes the microprocessor 281, a storage unit 282, a sensor driver 283, and a drive unit driver 284. The microprocessor 281 is connected to the microprocessor 251 of the measurement control unit 25 through the I/O interface 26. The microprocessor 281 thus can transmit and receive various data with the microprocessor 251 of the measurement control unit 25.

The storage unit 282 is configured by a ROM for storing control programs and the like for controlling the sub-detection unit 13, the preparation device unit 29, and the like, as well as a RAM or the like. The preparation device unit 29 includes the sample setting unit 2a, the sample pipette unit 11, the first dispersion unit 12, the discriminating/replacing unit 14, the container transfer unit 15, the second dispersion unit 16, the liquid removing unit 17, the reaction unit 18, the first reagent adding unit 19, the second reagent adding unit 20, the specimen aspirating unit 21, and the container washing unit 23.

The microprocessor 281 is connected to sensors and drive motors of each unit of the preparation device unit 29 through the sensor driver 283 or the drive unit driver 284. The microprocessor 281 thus can execute the control program based on the detection signal from the sensor to control the operation of the drive motor.

Figure 5:
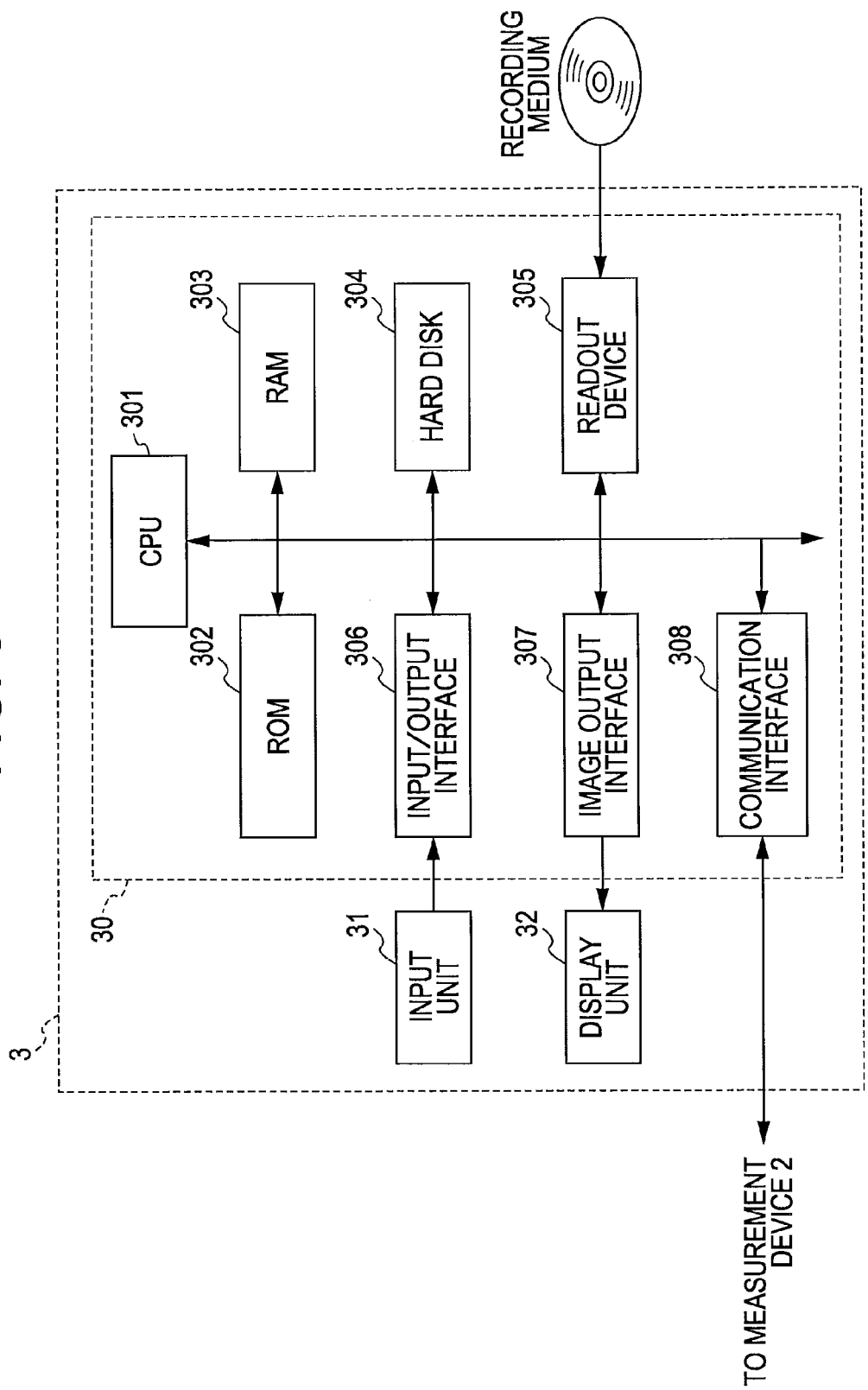
FIG. 5 is a view showing a configuration of a data processing device according to the present embodiment.

FIG. 5 is a view showing a configuration of a data processing device 3.

The data processing device 3 includes a personal computer, and is configured by a main body 30, an input unit 31, and a display unit 32. The main body 30 includes a CPU 301, a ROM 302, a RAM 303, a hard disc 304, a readout device 305, an input/output interface 306, an image output interface 307, and a communication interface 308.

The CPU 301 can execute computer programs stored in the ROM 302 and the computer programs loaded in the RAM 303. The RAM 303 is used to read out the computer programs recorded on the ROM 302 and the hard disc 304. The RAM 303 is also used as a work region of the CPU 301 when executing the computer programs.

The hard disc 304 is installed with various computer programs to be executed by the CPU 301 such as operating system and application program, and data used in execution of the computer programs. Specifically, the hard disc 304 is installed with programs and the like for analyzing the measurement result transmitted from the measurement device 2 and displaying on the display unit 32 based on the generated analysis result.

The CPU 301 executes the program installed in the hard disc 304 to acquire the characteristic parameters such as the forward scattered light intensity, the side fluorescence intensity and the like based on each signal FSC, SSC, SFL, and creates frequency distribution data for analyzing cells and nuclei based on the characteristic parameters. The CPU 301 then performs the discriminating processing of the particles in the measurement specimen based on the frequency distribution data, and determines whether or not the cell to be measured (epidermal cell) is abnormal, specifically, whether or not the cancerous cell (atypical cell). Such determination of the CPU 301 will be described later with reference to FIG. 9.

The read-out device 305 is configured by CD drive, DVD drive, and the like, and is able to read out computer programs and data recorded on a recording medium. The input unit 31 configured by a keyboard, and the like is connected to the input/output interface 306, where the operator uses the input unit 31 to input instruction and data to the data processing device 3. The image output interface 307 is connected to the display unit 32 configured with a display, or the like, and outputs an image signal corresponding to the image data is output to the display unit 32.

The display unit 32 displays an image based on the input image signal. The display unit 32 displays various types of program screens. The communication interface 308 can transmit and receive data to the measurement device 2.

Figure 6:
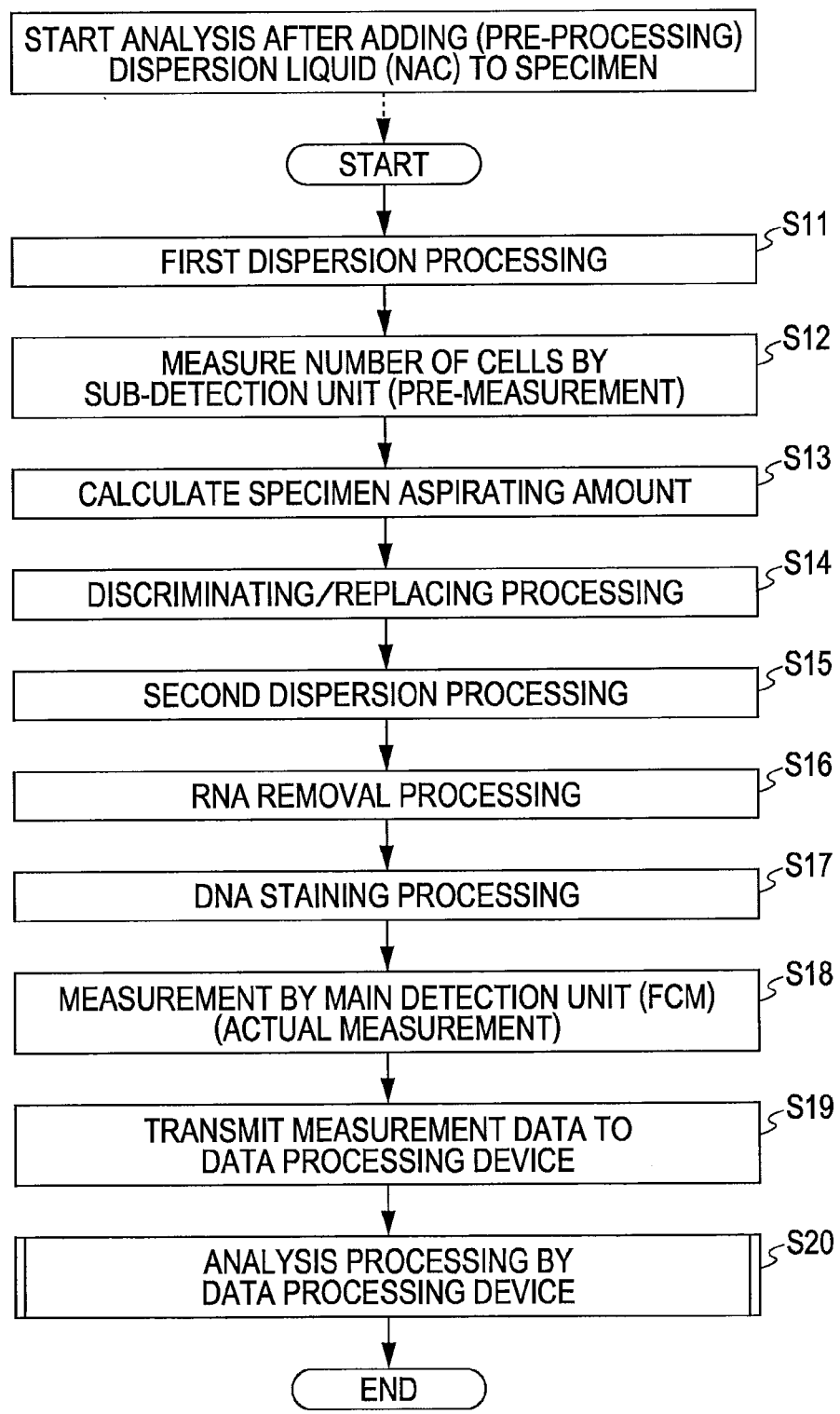
FIG. 6 is a flowchart showing an analyzing operation of the canceration information providing device according to the present embodiment.

FIG. 6 is a flowchart showing an analyzing operation of the canceration information providing device 1.

The operation control of the main detection unit 22 and the signal processing unit 24 of the measurement device 2 is executed by the microprocessor 251 of the measurement control unit 25. The operation control of the sub-detection unit 13, the signal processing unit 27, and the preparation device unit 29 of the measurement device 2 is executed by the microprocessor 281 of the preparation control unit 28. The control of the data processing device 3 is executed by the CPU 301.

In the analysis by the canceration information providing device 1, the specimen container 4 containing the biological specimen and the preservation solution having methanol as the main component is set in the sample setting unit 2a (see FIG. 2) by the operator, and then the analysis by the canceration information providing device 1 is started.

After the start of measurement, the dispersion process (first dispersion processing) of the aggregating cells in the specimen is carried out by the first dispersion unit 12 (S11). Specifically, the specimen in the specimen container 4 set in the sample setting unit 2a is aspirated by the sample pipette unit 11, and supplied into the specimen accommodating section 12a. The specimen supplied to the specimen accommodating section 12a is thereafter dispersed by the first dispersion unit 12.

After the first dispersion processing is finished, the dispersed specimen is supplied to the specimen retrieving section 13a of the sub-detection unit 13 by the sample pipette unit 11, and the dispersed specimen is flowed to the flow cell of the sub-detection unit 13 similar to the flow cell 43 of FIG. 3A by a predetermined amount. In the sub-detection unit 13, the detection (pre-measurement) of the number of normal cells contained in the specimen is carried out by the flow cytometry method (S12). The concentration of the specimen is calculated from the number of cells obtained by the pre-measurement and the volume of the specimen supplied to the sub-detection unit 13.

The aspiration amount of the specimen for preparing the measurement specimen to be used in the actual measurement is determined by the microprocessor 281 based on the calculated concentration (S13). In other words, the liquid amount of the specimen necessary for performing the actual measurement is calculated to an extent the significant number of cells is ensured based on the concentration of the specimen used in the pre-measurement (number of cells per unit volume) and the significant number of cells necessary for the cancerous cell detection in the actual measurement. In the present embodiment, for example, the number of single epidermal cells (significant number of cells) to supply to the flow cell 43 of the main detection unit 22 is assumed to be about twenty thousand. In this case, the specimen to supply to the discriminating/replacing unit 14 needs to include about a hundred thousand cells. Thus, the liquid amount of the specimen in S13 is calculated such that about a hundred thousand cells are supplied to the discriminating/replacing unit 14.

The single cells and aggregating cells of the cells to be measured (epidermal cells) coexist in the number of cells obtained with the pre-measurement, and white blood cells and the like other than the cells to be measured are also included. In other words, the obtained number of cells does not accurately indicate the number of cells to be measured. However, the significant number of cells required for the actual measurement can be accurately ensured to a certain extent by being based on the number of cells obtained with the pre-measurement.

The discriminating/replacing processing is then executed on the specimen of the calculated liquid amount (S14). In other words, the sample pipette unit 11 is driven by the preparation control unit 28, and the specimen after the first dispersion processing is aspirated from the specimen accommodating section 12a of the first dispersion unit 12 by the calculated liquid amount. The aspirated specimen is supplied to the discriminating/replacing unit 14 to start the discriminating/replacing processing.

The dispersion processing (second dispersion processing) of the aggregating cell in the specimen is then carried out by the second dispersion unit 16 (S15). Specifically, the container transfer unit 15 grips and takes out the measurement specimen container 5 set in the holder 18b of the reaction unit 18, and positions the measurement specimen container in the specimen exchanging section 11b. The specimen aspirated by the sample pipette unit 11 from the discriminating/replacing unit 14 is supplied to the measurement specimen container 5 positioned in the specimen exchanging section 11*b*. Thereafter, the measurement specimen container 5 is transferred to the second dispersion unit 16 by the container transfer unit 15, and the second dispersion processing is executed.

After the measurement specimen container 5 including the specimen performed with the second dispersion processing is set in the holder 18*b* of the reaction unit 18, the reagent (RNase) is added by the first reagent adding unit 19 and warmed by the reaction unit 18, so that the RNA removal processing of the cell to be measured in the measurement specimen container 5 is carried out (S16). After the RNA removal processing, the reagent (stain fluid) is added by the second reagent adding unit 20 and warmed by the reaction unit 18, so that the DNA staining processing of the cell to be measured in the measurement specimen container 5 is carried out (S17).

The measurement specimen performed with the DNA staining processing is aspirated by the specimen aspirating unit 21. The aspirated measurement specimen is fed to the flow cell 43 (see FIG. 3A) of the main detection unit 22, and the actual measurement on the cells in the measurement specimen is carried out (S18).

After the actual measurement, the obtained measurement data is transmitted from the measurement control unit 25 of the measurement device 2 to the data processing device 3 (S19). Specifically, the forward scattered light signal (FSC), the side scattered light signal (SSC), and the side fluorescence signal (SFL) obtained for each cell in the measurement specimen are transmitted to the data processing device 3. The CPU 301 of the data processing device 3 determines whether or not the measurement data is received from the measurement device 2 on a constant basis. When receiving the measurement data from the measurement device 2, the CPU 301 of the data processing device 3 performs the analysis processing based on the received measurement data (S20). The details of the analysis processing of S20 will be described later with reference to FIG. 9.

The procedure for acquiring the canceration information in the present embodiment will now be described.

Figure 7A:
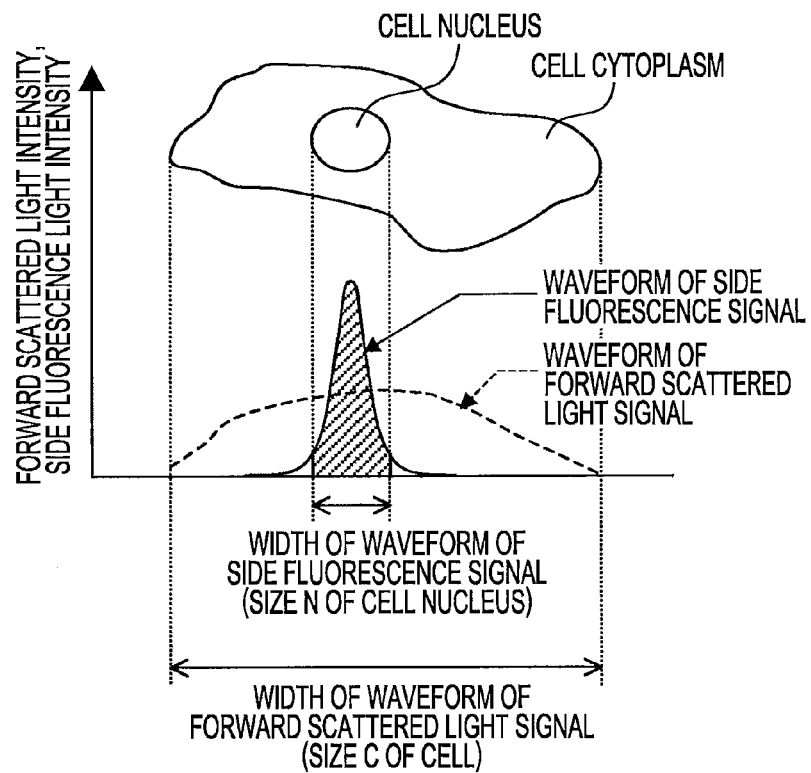
FIG. 7A is a view describing a forward scattered light signal and a side fluorescence signal according to the present embodiment.

FIG. 7A is a view describing the forward scattered light signal (FSC) and the side fluorescence light signal (SFL) obtained in the actual measurement (S18 of FIG. 6).

FIG. 7A shows a schematic view of the cell including the cell nucleus, and the waveform of the forward scattered light signal and the waveform of the side fluorescence light signal obtained from the cell. The vertical axis indicates the intensity of the light. The width of the waveform of the forward scattered light intensity represents the numerical value (size C of the cell) indicating the width of the cell. The width of the waveform of the side fluorescence intensity represents the numerical value (size N of the cell nucleus) indicating the width of the cell nucleus. As shown with shaded lines, the area of the region determined by the waveform of the side fluorescence intensity and a predetermined base line represents the amount of DNA of the cell.

Figure 7B:
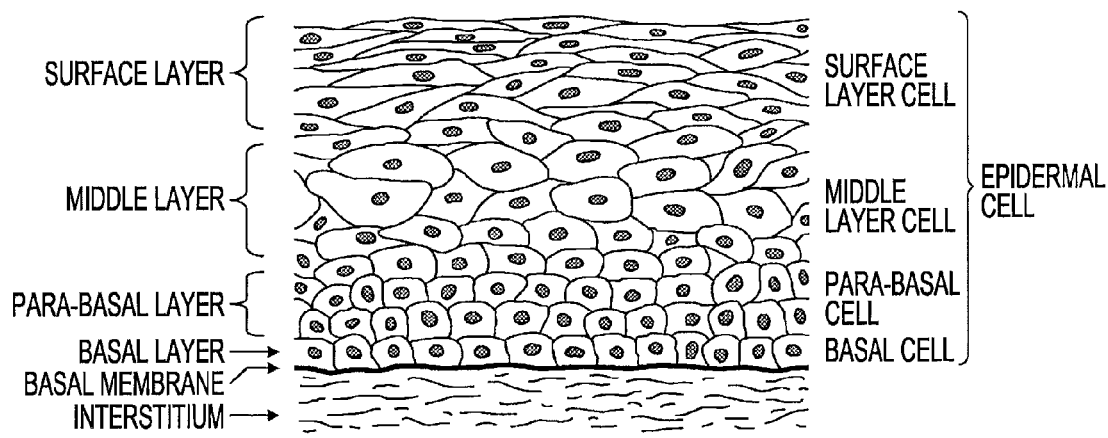
FIG. 7B is a view schematically showing an enlarged cross-section of epidermal cells of the uterine cervix.

FIG. 7B is a view schematically showing an enlarged cross-section of the epidermal cell of the uterine cervix.

In the uterine cervix, a layer (basal layer) formed by the basal cell, a layer (para-basal layer) formed by the para-basal cell, a layer (middle layer) formed by the middle layer cell, and a layer (surface layer) formed by the surface layer cell are formed in this order from the basal membrane side. The basal cell near the basal membrane is differentiated to the para-basal cell, the para-basal cell is differentiated to the middle layer cell, and the middle layer cell is differentiated to the surface layer cell.

The cell related to the canceration of the epidermal cells is the basal cell in the epidermal cells of the uterine cervix. In the process of becoming a cancer, the basal cell acquires the atypical formation and becomes the atypical cell. The atypical cell acquires the ability to proliferate, and occupies from the basal layer side to the surface layer side. Thus, in the initial stage to becoming a cancer, a great number of cancerous cells exist in the cells existing in the basal layer, the para-basal layer, and the middle layer in the epidermal cells of the uterine cervix. In the initial stage to becoming a cancer, the cancerous cells are extremely few in the cells existing on the surface layer side of the epidermal cells of the uterine cervix.

Figure 7C:
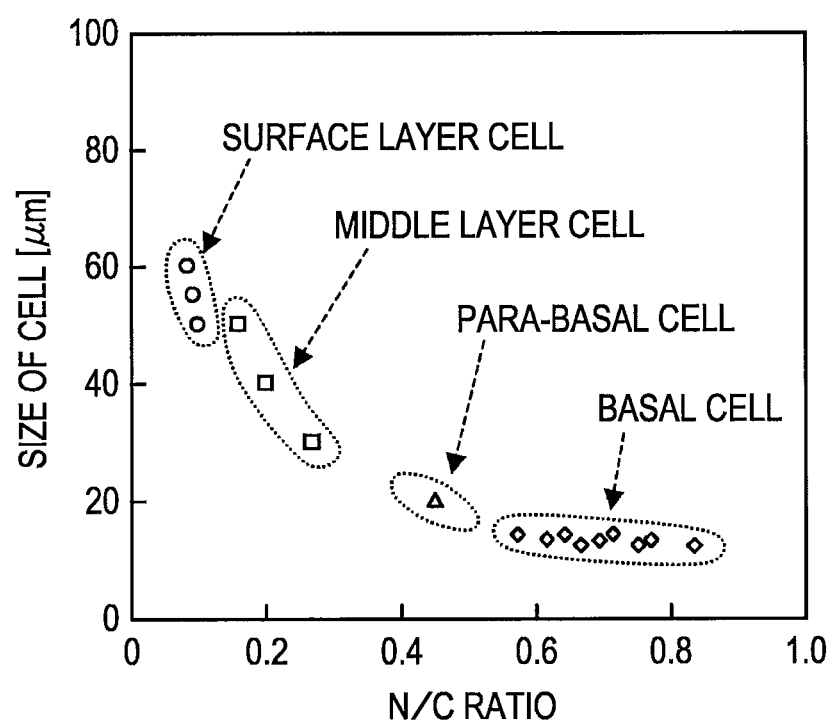
FIG. 7C is a view showing a relationship between the N/C ratio and the size of the cell.

In the epidermal cell, the size of the cell sequentially becomes smaller but the size of the cell nucleus sequentially becomes larger from the layer on the surface layer side toward the layer on the basal membrane side. Therefore, the ratio (hereinafter also referred to as "N/C ratio") of the size (N) of the cell nucleus with respect to the size (C) of the cell also sequentially becomes larger from the layer on the surface layer side toward the layer on the basal membrane side. Thus, the N/C ratio and the size C of the cell are in a relationship shown in FIG. 7C, for example. Thus, the para-basal cell and the basal cell can be extracted by extracting the cell having a large N/C ratio.

Figure 8A:
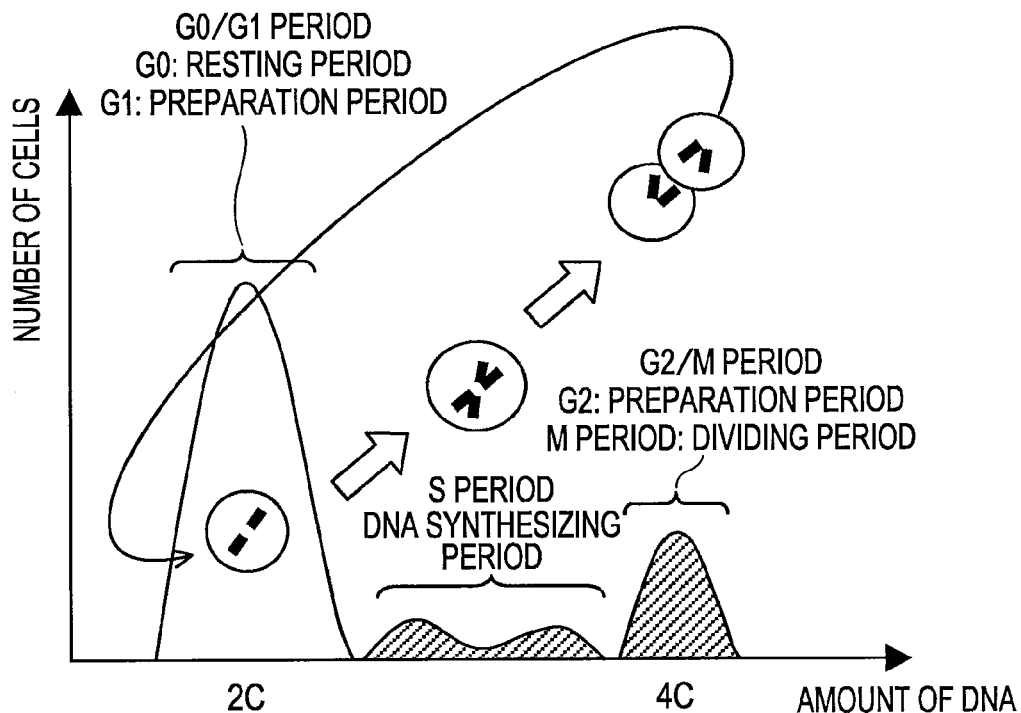
FIG. 8A is a view showing a relationship of the amount of DNA and the number of cells in the cell cycle according to the present embodiment.

FIG. 8A is a view showing a relationship of the amount of DNA and the number of cells in the cell cycle.

The cell becomes two cells and returns to the starting point through events such as DNA replication, distribution of chromosome, nuclear division, cytoplasmic division, and the like according to a certain cycle (cell cycle). The cell cycle can be divided to four periods according to the stage, a G1 period (timing of preparation and inspection to enter S period), S period (DNA synthetic period), G2 period (timing of preparation and inspection to enter M period), and M period (mitotic period). If G0 period (resting period) in which the proliferation of the cell is resting is added to the four periods, the cell is in one of the stages of the five periods.

Figure 8B:
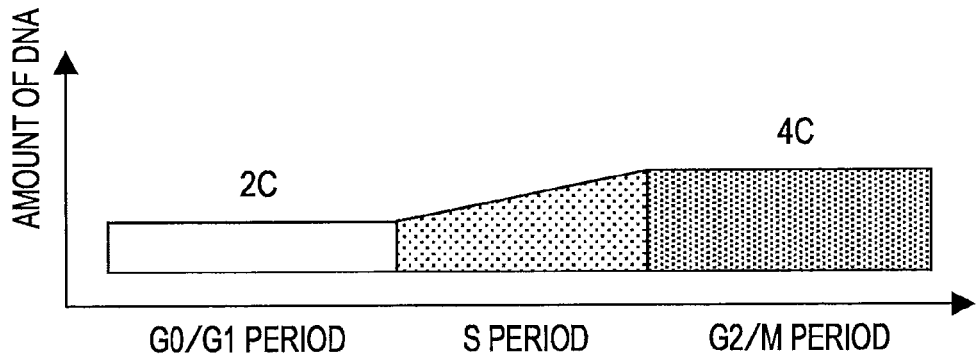
FIG. 8B is a view showing an amount of DNA that changes for every cell cycle.

When the cell proliferates according to the cell cycle, the chromosome of the nucleus in the cell also increases, and hence in what state of the cell cycle the cell is in can be estimated by measuring the amount of DNA of the cell. If the case of a normal cell, the amount of DNA in the G0/G1 period is a constant value (2C), the amount of DNA gradually increases in the following S period, the amount of DNA is a constant value (4C) in the G2 period, and such value is maintained in the M period, as shown in FIG. 8B. C refers to the genomic DNA content per haploid. In other words, 2C is the amount of DNA of two times the genomic DNA content per haploid, and 4C is the amount of DNA of four times the genomic DNA content per haploid. The amount of DNA of the normal cell in the G0 period or the G1 period of the cell cycle is 2C. When a histogram of the amount of DNA is created for the normal cell, a histogram shown in FIG. 8A is obtained. A hill having the highest peak corresponds to the cell in the G0/G1 period in which the amount of DNA is the least, a hill having the second highest peak corresponds to the cell in the G2/M period in which the amount of DNA is the largest, and in between corresponds to the cell in the S period.

In the case of normal cells, the number of cells in the state of the S period and the G2/M period is extremely small compared to the number of cells in the G0/G1 period.

However, in the case of cancerous cells, the number of cells in the state of the S period and the G2/M period is greater than the normal cells. In the case of cancerous cells, the number of chromosomes of the cell increases, and hence the amount of DNA increases.

In the present embodiment, two determination methods (determinations 1, 2) focusing on the N/C ratio and the amount of DNA are used for the determination of canceration. In the "analysis processing by the data processing device 3" (S20 of FIG. 6), the determination of canceration is carried out based on the determinations 1, 2.

In determination 1, the cell having a large N/C ratio is extracted to extract the basal cell, the para-basal cell, and the middle layer cell in which canceration is assumed to advance easily. Then, the cell having a large amount of DNA is extracted from the extracted cell group to effectively extract the cell having a high possibility of being the cancerous cell (second counting step). In determination 1, the possibility of canceration is determined to be high when the number of cells obtained by the second counting step is large.

In determination 2, the cell having a small N/C ratio is extracted to extract the middle layer cell and the surface layer cell in which canceration is assumed to advance with difficulty. Then, the cell having a small amount of DNA is extracted from the extracted cell group to effectively extract the cell having a low possibility of being the cancerous cell (first counting step). Generally, when the canceration of the tissue advances, the number of cells obtained by the second counting step increases, and the number of cells obtained by the first counting step decreases. Thus, the ratio of both numbers of cells greatly differs between when the tissue is normal and when the tissue has become cancerous. In determination 2, the canceration of the tissue is determined based on such ratio. Thus, through the use of the ratio of two numbers of cells in which the increasing/decreasing tendency are opposite to each other, the determination result of high reliability can be obtained even if the cell to be measured contained in the measurement specimen is relatively few.

Figure 9:
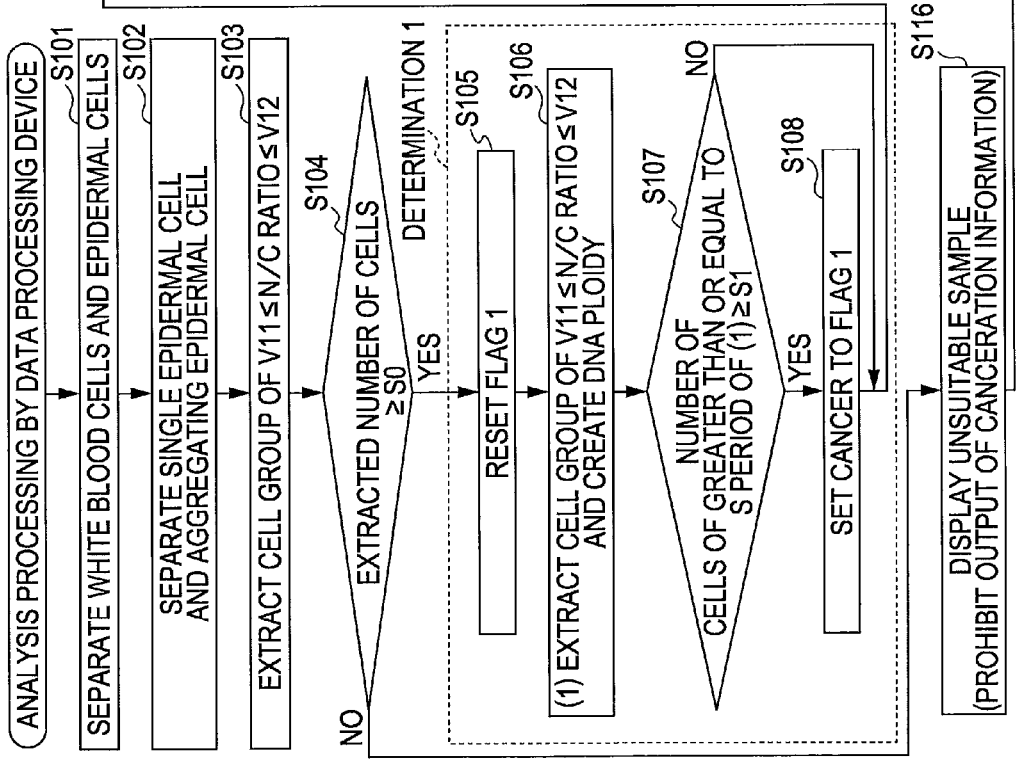
FIG. 9 is a flowchart showing an analysis processing in the data processing device according to the present embodiment.

FIG. 9 is a flowchart showing an analysis processing in the data processing device 3.

The CPU 301 of the data processing device 3 creates a scattergram shown in FIG. 10A when receiving measurement data from the measurement device 2. In FIG. 10A, the horizontal axis represents the size of the cell (width of the waveform of the forward scattered light signal), and the vertical axis represents the amount of DNA (sum of the waveform of the side fluorescence signal).

The CPU 301 then separates the white blood cells and the epidermal cells (S101). Specifically, the CPU 301 sets a region A1 in which lower left region corresponding to the white blood cells is lacking in the scattergram of FIG. 10A and extracts the cells contained in the region A1

The CPU 301 then creates a scattergram shown in FIG. 10B from the cell group extracted in S101. In FIG. 10B, the horizontal axis represents (differential sum of side fluorescence signal/peak value of side fluorescence signal), and the vertical axis represents (differential sum of forward scattered light signal/peak value of forward scattered light signal).

The CPU 301 then separates the single epidermal cell and the aggregating epidermal cells (S102). Specifically, the CPU 301 sets a region A2 corresponding to the single epidermal cell in the scattergram of FIG. 10B, and extracts the cells contained in the region A2. The removal of the aggregating cells is carried out to prevent lowering of analysis precision that occurs when the measurement amount of DNA indicates an abnormal value when a plurality of cells aggregate although the amount of DNA is normal as a single cell.

The CPU 301 then creates a scattergram shown in FIG. 10C from the cell group extracted in S102. In the histogram of FIG. 10C, the horizontal axis represents the value (N/C ratio) obtained by dividing the size N of the cell nucleus by the size C of the cell, and the vertical axis represents the size of the cell.

The CPU 301 then extracts the cell group of V11≤N/C ratio≤V12 in the histogram of FIG. 10C (S103). Specifically, the CPU 301 sets a region A4 in the scattergram of FIG. 10C, and extracts the cells contained in the region A4. The value on the left end and the value on the right end of the region A4 are such that the value of N/C ratio is set to V11, V12. V11 is a threshold value that divides the middle layer cell and the para-basal cell. V11 is appropriately set from the standpoint of sensitivity and specificity. In the present embodiment, V11 is set within a range of 0.2 to 0.4. V12 is a threshold value that divides the basal cell and the insignificant cell. V12 is appropriately set from the standpoint of sensitivity and specificity. In the present embodiment, V12 is set within a range of 0.6 to 1.

Figure 11B:
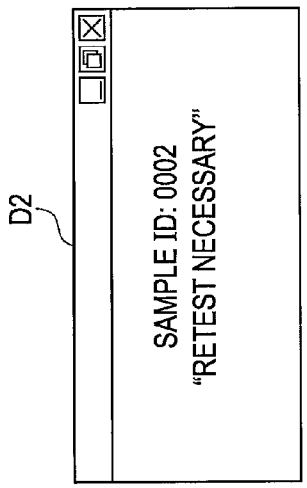
FIGS. 11A-11D are views showing dialogues displayed on the display unit according to the present embodiment.
Figure 11D:
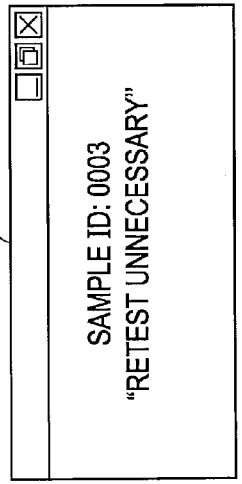
Figure 11A:
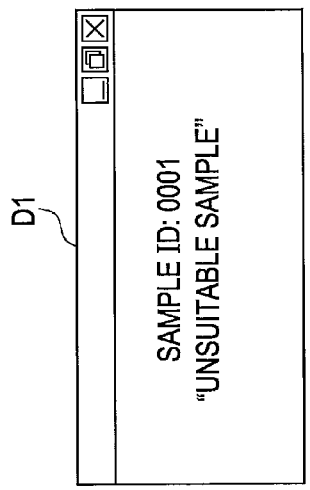

The CPU 301 then determines whether or not the number of cells extracted in S103 is greater than or equal to the threshold value S0 (S104). If the number of cells is insufficient, the determination accuracy of canceration may lower. Therefore, if the number of cells is smaller than the threshold value S0 (S104: NO), the CPU 301 displays a notification that the sample is an unsuitable sample (S116). Specifically, as shown in FIG. 11A, the CPU 301 displays a dialogue D1 displayed as "unsuitable sample" on the display unit 32. In this case, a message such as "NG", "non-analyzable", and the like may be displayed in the dialogue D1. The CPU 301 terminates the processing without outputting the canceration information. The threshold value S0 is a threshold value for determining the unsuitability of collecting the sample. The threshold value S0 is appropriately set from the standpoint of sensitivity and specificity. In the present embodiment, the threshold value S0 is set within a range of 50 to 1000.

If the number of cells extracted in S103 is greater than or equal to the threshold value S0 (S104: YES), the CPU 301 resets the value of the flag 1 stored in the hard disc 304 (S105). The flag 1 is provided to indicate the determination result by the "determination 1", described above. The CPU 301 then extracts the cell group of V11÷N/C ratio≤V12 in the scattergram of FIG. 10C, similar to S103, and creates a histogram (DNA ploidy) shown in FIG. 10D (S106). In the histogram of FIG. 10D, the horizontal axis represents the amount of DNA and the vertical axis represents the number of cells.

The CPU 301 then determines whether the number of cells in which the amount of DNA is greater than or equal to the S period of the normal cell, that is, the number of cells having the amount of DNA exceeding the amount of DNA of the normal cell in which the cell cycle is the G0 period or the G1 period is greater than or equal to a threshold value S1 in the histogram created in S106 (S107). Specifically, the CPU 301 sets a region A5 in the histogram shown in FIG. 10D, and determines whether or not the number of cells contained in the region A5 is greater than or equal to the threshold value S1. A value V21 at the left end of the region A5 is set to become the upper limit value of the range of the amount of DNA detected as the amount of DNA of the normal cell in which the cell cycle is in the G0/G1 period in the canceration information providing device 1. The right end of the region A5 is set to include all the cells in the right direction. The threshold value Si of the number of cells used in the determination of the number of cells is determined in correspondence with the single epidermal cell supplied to the flow cell 43 of the main detection unit 22 being about twenty thousand. The threshold value S1 is a threshold value for fractionating the cancer sample and the negative sample. The threshold value S1 is appropriately set from the standpoint of sensitivity and specificity as it differs depending on the number of measured cells. In the present embodiment, the threshold value S1 is set within a range of 2000 to 4000.

If the number of cells contained in the region A5 is greater than or equal to the threshold value S1 (S107: YES), the CPU 301 sets "Cancer" to the flag 1 (S108). If the number of cells contained in the region A5 is smaller than the threshold value S1 (S107: NO), S108 is skipped. The processing of S105 to S108 correspond to the "determination 1" described above.

The CPU 301 then resets the value of the flag 2 stored in the hard disc 304 (S109). The flag 2 is provided to indicate the determination result by the "determination 2", described above. The CPU 301 then extracts the cell group of V13≤N/C ratio≤V11 (cell group contained in the region A3) in the scattergram of FIG. 10C, and creates a histogram (DNA ploidy) shown in FIG. 10E (S110). V13 is a threshold value to have the surface layer cell or the middle layer cell contained in the range of V13≤N/C ratio≤V11. V13 is appropriately set from the standpoint of sensitivity and specificity. In the present embodiment, V13 is set within a range of smaller than V11 and greater than or equal to 0. In the histogram of FIG. 10E, the horizontal axis represents the amount of DNA and the vertical axis represents the number of cells.

The CPU 301 then obtains the number of cells in which the amount of DNA is 2C of the normal cells, that is, the number of cells having the amount of DNA of the normal cell in which the cell cycle is the G0 period or the G1 period in the histogram created in S110. Specifically, the CPU 301 sets a region A6 in the histogram shown in FIG. 10E, and obtains the number of cells contained in the region A6. The value V32 at the right end of the region A6 is set to be the same as the value V21 at the left end of the region A5.

The V32 (V21) set herein is set as a value for dividing the amount of DNA (2C) of the normal cell in the G0 period or the G1 period and the amount of DNA of the normal cell in the S period. Specifically, V30 indicating the amount of DNA of the normal cell in which the cell cycle is in the G0 period or the G1 period is set, where V31 and V32 (V21) are set such that V30 is within the range of V31 and V32 (V21) and the width of the range of V31 and V32 is A.

The CPU 301 then obtains a value (hereinafter referred to as "canceration ratio") obtained by dividing the number of cells in which the amount of DNA is greater than or equal to the S period of the normal cell in the histogram created in S106, that is, the number of cells having the amount of DNA exceeding the amount of DNA of the normal cell in which the cell cycle is in the G0 period or the G1 period by the number of cells in which the amount of DNA is 2C in the histogram created in S110, that is, the number of cells having the amount of DNA of the normal cell in which the cell cycle is in the G0 period or the G1 period. The CPU 301 then determines whether or not the canceration ratio is greater than or equal to a predetermined threshold value S2 (S111). If the canceration ratio is greater than or equal to the threshold value S2 (S111: YES), the CPU 301 sets "Cancer" to the flag 2 (S112). If the canceration ratio is smaller than the threshold value S2 (S111: NO), S112 is skipped. The processing of S109 to S112 correspond to the "determination 2" described above. The threshold value S2 is a threshold value for fractionating the cancer sample and the negative sample. The threshold value S2 is appropriately set from the standpoint of sensitivity and specificity. In the present embodiment, the threshold value S2 is set within a range of 0.5 to 1.5.

Figure 11C:
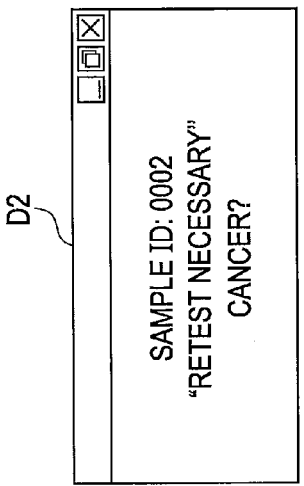

If "Cancer" is set to one of the flags 1, 2 (S113: YES), that is, if determined as "Cancer" in determination 1 or determination 2, the CPU 301 displays a notification that retest is necessary as information relating to canceration (S114). Specifically, as shown in FIG. 11B, the CPU 301 displays a dialogue D2 displayed as "retest necessary" on the display unit 32. In this case, display "Cancer?" may be added to the dialogue D2 to indicate that the suspicion of canceration is high, as shown in FIG. 11C.

If both flags 1, 2 do not indicate "Cancer" (S113: NO), that is, if determination is not made as "Cancer" in both determinations 1, 2, the CPU 301 displays a notification that retest is not necessary (S115). Specifically, as shown in FIG. 11D, the CPU 301 displays a dialogue D3 displayed as "retest unnecessary" on the display unit 32.

If the significant number of cells necessary for cancerous cell detection cannot be ensured because the biological specimen contained in the specimen container 4 is insufficient, an appropriate result may not be obtained in the determination 1. In this case, whether or not "Cancer" may be determined based only on the value of the flag 2 in S113.

FIGS. 12A to 12E are scattergrams of five samples in which the degree of advancement of the cancer differs. FIGS. 12A to 12E correspond to "Cancer", "CIN3", "CIN2", "CIN1", "Normal" indicating the degree of advancement of the cancer. As the cancer advances from "Normal" to "Cancer", the number of cells contained in the region A4 in which the N/C ratio is large becomes greater compared to the number of cells contained in the region A3 in which the N/C ratio is small.

FIGS. 13A to 13E are histograms created by extracting the cell group contained in the region A4 of high N/C ratio of FIGS. 12A to 12E. Here, the region A5 corresponding to the amount of DNA of greater than or equal to the S period of FIGS. 13A to 13E contain 6785, 875, 4042, 589, and 121 cells, respectively. In this case, by setting the value of the threshold value S0 to 100 and the value of the threshold value S1 to between 875 and 4042, the samples of FIGS. 13A and 13C are determined as "Cancer" and the samples of FIGS. 13B, 13D, and 13E are not determined as "Cancer" in the determination 1 of FIG. 9. In this case, the samples of FIGS. 13A, 13B, 13D, and 13E are appropriately determined whether cancer or not in the determination 1, but the sample of FIG. 13C is not appropriately determined whether or not cancer in the determination 1.

FIGS. 14A to 14E are histograms created by extracting the cell group contained in the region A4 of low N/C ratio of FIGS. 12A to 12E. Here, the region A6 corresponding to the amount of DNA of 2C of FIGS. 14A to 14E contain 738, 1878, 8270, 28787, and 19485 cells, respectively. The canceration ratio obtained in S111 of FIG. 9 thus becomes 9.19, 0.47, 0.49, 0.02, 0.01 in the samples of FIGS. 14A to 14E, respectively. In this case, by setting the value of the threshold value S0 to 100 and the value of the threshold value S2 to between 0.49 and 9.19, the sample of FIG. 14A is determined as "Cancer" and the samples of FIGS. 14B to 14E are not determined as "Cancer" in the determination 2 of FIG. 9. Therefore, in this case, the samples of FIGS. 14A to 14E are all appropriately determined whether cancer or not in the determination 2.

FIGS. 15A to 15C are views describing a relationship of the determination result of the tissue diagnosis and the determination result by the determination 1 of FIG. 9. The determination is made on 1035 samples.

The region A11 on the left side of FIG. 15A is a boxplot showing variation and the like of data, and the region A12 on the right side is a histogram. In regions A11, A12, the five values on the horizontal axis correspond to "Normal", "CIN1", "CIN2", "CIN3", and "Cancer" of the result of tissue diagnosis from the left. The vertical axis of FIG. 15A shows the number of cells greater than or equal to the amount of DNA of the normal cell in the S period counted in S107 of FIG. 9.

In the region A11 of FIG. 15A, one dot corresponds to one sample. Each sample diagnosed as "Normal" in the tissue diagnosis is plotted to a position of the corresponding number of cells (vertical axis) in the leftmost column. For example, with respect to the sample diagnosed as "Normal", if the number of cells greater than or equal to the amount of DNA of the normal cell in the S period counted in S107 of FIG. 9 is smaller than the threshold value S1, such sample is plotted to a position corresponding to such number of cells in the vertical axis direction of the leftmost column ("Normal" column). Similarly, each sample diagnosed as "CIN1", "CIN2", "CIN3", and "Cancer" is plotted to a position corresponding to the number of cells in the vertical axis direction in a row of corresponding canceration stage. The region A12 of FIG. 15A represents a bar graph where in what proportion the samples contained in each canceration stage are distributed on the vertical axis is shown. FIG. 15A shows the position of the threshold value S1 of the number of cells set in S107 of FIG. 9 with a dotted line. In other words, the sample plotted to a position of greater number of cells than the dotted line is determined as "Cancer" in the determination 1 of FIG. 9.

With reference to FIG. 15A, one sample determined as "Cancer" in the determination 1, that is, one positive sample in which the number of cells of greater than or equal to the amount of DNA of the normal cell in the S period is greater than or equal to the threshold value S1 exists in the samples determined as "Normal" by the tissue diagnosis. The sample determined as "CIN1" by the tissue diagnosis is recognized as all being appropriately determined as "Normal" in the determination 1. Two samples determined as "Cancer" in the determination 1 exist respectively in the samples determined as "CIN2" and "CIN3" by the tissue diagnosis. The sample determined as "Cancer" by the tissue diagnosis is recognized as all being appropriately determined as "Cancer" in the determination 1.

FIG. 15B shows a table summarizing the content of FIG. 15A. In the items of the tissue diagnosis, positive means that the sample is cancerous and negative refers to sample of CIN3 or lower. In the item of the determination 1, positive refers to sample determined as YES in S107 of FIG. 9, and negative refers to sample determined as NO in S107 of FIG. 9.

With reference to FIG. 15B, the samples determined as positive in the tissue diagnosis are six among the 11 samples determined as positive in the determination 1. In other words, five samples are false positive (different from tissue diagnosis) according to the determination 1. The 1024 samples determined as negative by the determination 1 are all diagnosed as negative in the tissue diagnosis.

FIG. 15C shows the determination result of FIG. 15B in percentage.

Since all six samples, which were positive in the tissue diagnosis, are determined as positive according to the determination 1, the sensitivity according to the determination 1 is 6/6=100.0%. Furthermore, since 1024 samples are determined as negative out of the 1029 samples, which were negative in the tissue diagnosis, according to the determination 1, the specificity according to the determination 1 is 1024/1029=99.5%.

FIGS. 16A to 16C are views describing a relationship of the determination result of the tissue diagnosis and the determination result according to the determination 2 of FIG. 9, similar to FIGS. 15A to 15C. The vertical axis of FIG. 16A represents the canceration ratio (ratio obtained in S111) obtained with the determination 2 of FIG. 9. FIG. 16A shows the position of the threshold value S2 of the canceration ratio set in S111 of FIG. 9 with a dotted line. In other words, the sample plotted to a position of higher canceration ratio than the dotted line is determined as "Cancer" in the determination 2 of FIG. 9.

With reference to FIG. 16A, eight samples determined as "Cancer" in the determination 2, that is, eight positive samples in which the canceration ratio is greater than or equal to the threshold value S2 exists in the samples determined as "Normal" by the tissue diagnosis. The samples determined as "CIN1" and "CIN2" by the tissue diagnosis are recognized as all being appropriately determined as "Normal" in the determination 2. One sample determined as "Cancer" in the determination 2 exists in the samples determined as "CIN3" by the tissue diagnosis. One sample not determined as "Cancer" in the determination 2, that is, inappropriately determined as not "Cancer" where it is to be actually determined as "Cancer" exists in the samples determined as "Cancer" by the tissue diagnosis.

FIG. 16B shows a table summarizing the content of FIG. 16A, similar to FIG. 15B.

With reference to FIG. 16B, five samples are determined as positive in the tissue diagnosis among the 14 samples determined as positive in the determination 2. In other words, nine samples are false-positive (different from tissue diagnosis) according to the determination 2. 1020 samples, which were negative in the tissue diagnosis, exist in the 1021 samples determined as negative according to the determination 2. In other words, one sample is false-negative (different from tissue diagnosis) according to the determination 2.

FIG. 16C shows the determination result of FIG. 16B in percentage.

Since five samples out of six samples, which were positive in the tissue diagnosis, are determined as positive in the determination 2, the sensitivity according to the determination 2 is 5/6=83.3%. Since 1020 samples out of 1029 samples, which were negative in the tissue diagnosis, are determined as negative, according to the determination 2, the specificity according to the determination 2 is 1020/1029=99.1%.

As shown in the present embodiment, when performing the determination of "Cancer" by combining the determinations 1, 2 in S113 of FIG. 9, the relationship of the determination result of the tissue diagnosis and the determination result of S113 of FIG. 9 is as shown in FIGS. 16D and 16E.

With reference to FIG. 16D, six samples are determined as positive in the tissue diagnosis among the 18 samples determined as positive in S113. In other words, 12 samples are false positive (different from tissue diagnosis) according to the determination of S113. 1017 samples determined as negative according to the determination of S113 are all actually negative.

With reference to FIG. 16E, all six samples, which were positive in the tissue diagnosis, are determined as positive according to the determination of S113, and hence the sensitivity according to S113 is 6/6=100.0%. Furthermore, since 1017 samples are determined as negative out of the 1029 samples, which were negative in the tissue diagnosis, according to the determination of S113, the specificity according to S113 is 1017/1029=98.8%.

According to the present embodiment, whether or not it is cancer can be determined according to the determination 1 of FIG. 9. According to the determination 1, five samples out of 1029 negative samples are false positive, but all six samples determined as "Cancer" in the tissue diagnosis can be appropriately determined as "Cancer", as described with reference to FIGS. 15A to 15C.

In the determination 1, the cell group in which the amount of DNA is greater than or equal to V21 is extracted out of the cell groups in which the N/C ratio is V11 to V12. Since it is limited to a range in which the N/C ratio of the cell to extract is high, the determination accuracy according to the determination 1 can be enhanced.

In the determination 1, the concentration detection (pre-measurement) is carried out in the sub-detection unit 13, and the specimen necessary to an extent the significant number of cells necessary for the cancerous cell detection can be ensured is supplied to the main detection unit 22. Thus, whether or not it is cancer can be accurately determined by comparing the number of cells of greater than or equal to the amount of DNA of the normal cell in the S period and a predetermined number (S1) in S107 of FIG. 9.

According to the present embodiment, whether or not it is cancer can be determined according to the determination 2 of FIG. 9. According to the determination 2, nine samples out of 1029 negative samples are false positive and one sample out of six positive samples is false negative, but most of the samples determined as Cancer in the tissue diagnosis is appropriately determined as "Cancer", as described with reference to FIGS. 16A to 16C.

According to the present embodiment, if determination is made as "Cancer" in one of the determinations 1, 2 in S113 of FIG. 9, determination is made as "Cancer" as a final result, and this is notified to the operator. Thus, even if the result of one of the determinations 1, 2 includes false negative sample, determination is made as "Cancer" as a result if determined as "Cancer" in the other determination, and hence the sample to be determined as "Cancer" can be reliably determined as "Cancer".

In the present embodiment, the determinations 1, 2 are performed in parallel, and the results of the determinations 1, 2 are determined in S113 of FIG. 9 to ultimately determine whether or not it is "Cancer", but the final determination can be carried out using only one of the determinations 1, 2.

Figure 17A:
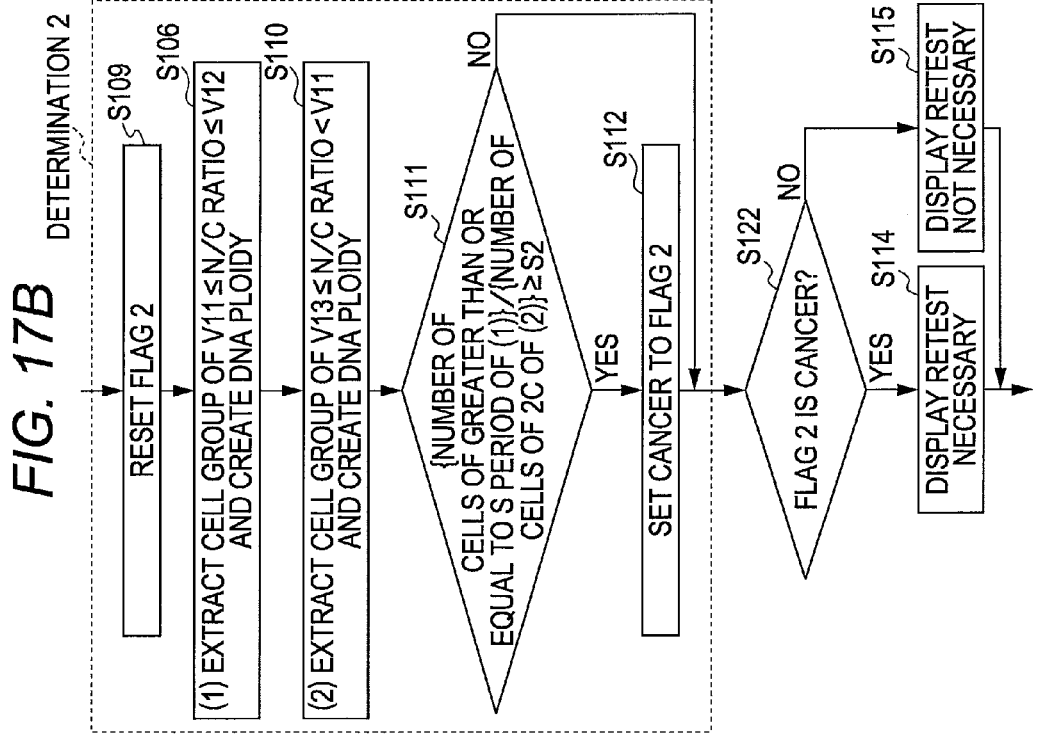
FIGS. 17A and 17B are flowcharts showing a variant of the analysis processing in the data processing device according to the present embodiment.
Figure 17B:
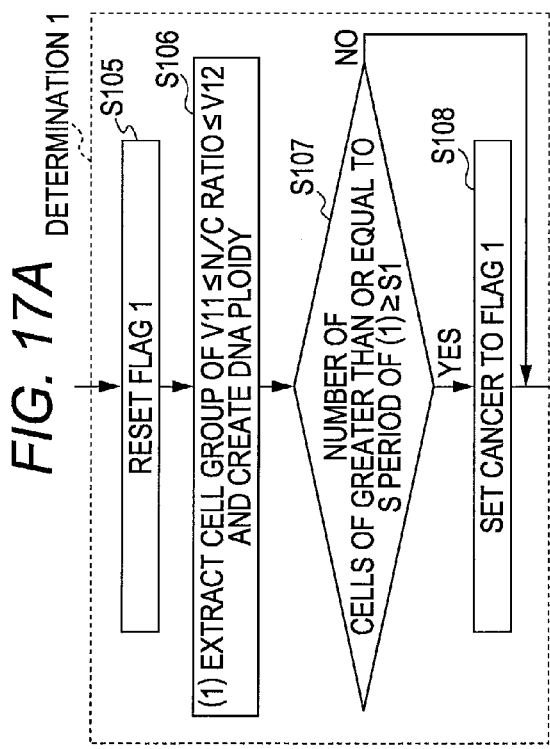

FIG. 17A is a view showing a case in which only the determination 1 is used. FIG. 17B is a view showing a case in which only the determination 2 is used. In FIGS. 17A and 17B, the same number is denoted on the area same as the processing of FIG. 9, and only the vicinity of the determinations 1, 2 is shown.

In FIG. 17A, after the determination 1 similar to FIG. 9 is performed, the CPU 301 of the data processing device 3 determines whether or not the flag 1 is "Cancer" (S121). In FIG. 17B, after the determination 2 similar to FIG. 9 is performed, the CPU 301 determines whether or not the flag 2 is "Cancer" (S122). When the final determination is performed as in FIGS. 17A and 17B, the determination result of FIGS. 15A to 15C and the determination results of FIGS. 16A to 16C respectively become the final determination. When the determination is performed as in FIGS. 17A and 17B, the effects similar to the determinations 1, 2 described above are respectively obtained.

In the present embodiment, the white blood cells and the epidermal cells (single epidermal cell, aggregating epidermal cells) are separated in S101 of FIG. 9. The determination accuracy of canceration of the epidermal cell to be measured thus can be improved. In the present embodiment, the single epidermal cell and the aggregating epidermal cells are separated in S102 of FIG. 9. The determination accuracy of canceration of the epidermal cells to be measured thus can be improved.

In the present embodiment, "unsuitable sample" is displayed when determined as NO in S104 of FIG. 9, and the processing is terminated. Therefore, when the number of extracted cells is few and the appropriate determination cannot be made as well, the output of the information related to the canceration of the cells is prohibited, so that the information of low reliability can be prevented from being output in advance and an appropriate diagnosis can be smoothly carried out. In this case, information notifying that the number of cells to be measured is insufficient is also desirably output. Measures such as recollecting the epidermal cells, and the like then can be smoothly carried out.

The embodiment of the present invention has been described above, but the present invention is not limited to such embodiment. The embodiment of the present invention can be modified in various ways.

For example, in the embodiment described above, the epidermal cells of the uterine cervix are the target of analysis, but other epidermal cells of buccal cells, bladder, pharynges, and the like, and furthermore, the epidermal cells of the organs may be the target of analysis, and the determination on the canceration of the cells may be carried out.

In the embodiment described above, the detection of the number of cells (pre-measurement) is carried out in the sub-detection unit 13, but the sub-detection unit 13 may be omitted if variation in the concentration of the cell to be measured is small for each biological specimen, and the influence on the analysis is small.

In the embodiment described above, the N/C ratio is calculated as a ratio of the numerical value (size N of cell nucleus) indicating the width of the cell nucleus obtained based on the width of the waveform of the side fluorescence intensity and the numerical value (size C of cell) indicating the width of the cell obtained based on the width of the waveform of the forward scattered light intensity. However, this is not the sole case, and the N/C ratio may be calculated as a ratio of the area of the cell nucleus and the area of the cell. In the embodiment described above, the numerical value (size C of cell) indicating the width of the waveform of the forward scattered light intensity is obtained. Thus, the size of the cell can be accurately expressed even if a cell having a long shape flows through the flow cell in a predetermined direction.

Figure 18A:
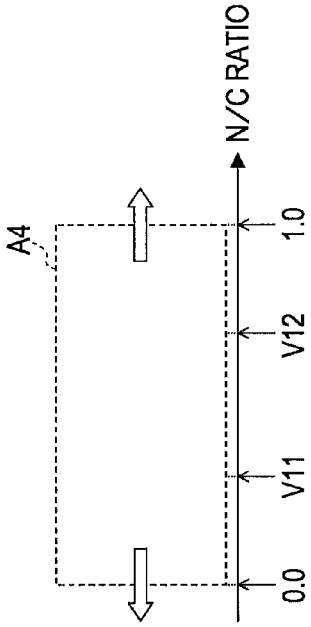
FIGS. 18A-18D are views showing a variant of a region set in the scattergram and the histogram according to the present embodiment.
Figure 18B:
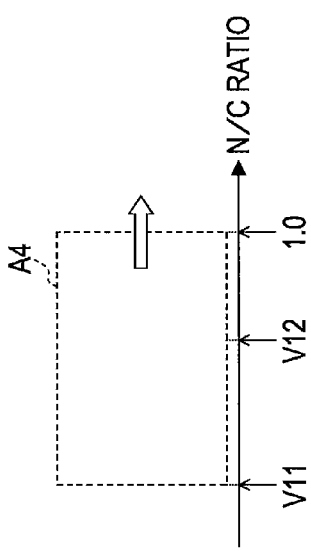

FIG. 18A is a view showing a state in which the upper limit of the extracting range of the cell group in S106 of FIG. 9 is removed, that is, a state in which the boundary on the right side of the region A4 of FIG. 10C is extended in the right direction. FIG. 18B is a view showing a state in which both the upper limit and the lower limit of the extracting range (region A4) of the cell group in S106 of FIG. 9 are removed.

When the region A4 is set as in FIGS. 18A and 18B, and the determination on canceration is carried out for 1035 samples similar to the above, the sensitivity is 83.3%, similar to the embodiment described above, and the specificity is 94.6% and 93.3% in the determination 2, which is only slightly lower than the embodiment described above. Therefore, determination can be appropriately made as "Cancer", similar to the embodiment described above, even if the range of cells to extract is extended. Accordingly, the sensitivity and the specificity are known by analogy to be maintained similarly for the determination 1 when the region 4 is set as in FIGS. 18A and 18B.

In the embodiment described above, the value at the left end of the region A5 for setting the amount of DNA greater than or equal to the amount of DNA of the normal cell in the S period shown in FIG. 10D is set to V21, and the value at the right end is set to include all the cells of greater than or equal to the amount of DNA of the normal cell in the S period, but the minimum value and the maximum value of such set range are not fixed to the above, and may be appropriately set to values other than the above to enhance sensitivity and specificity. The values at the left end and the right end of the region A6 for setting the amount of DNA of 2C shown in FIG. 10E are respectively set to V31, V32, but the minimum value and the maximum value of such set range are not fixed to V31 and V32, and may be appropriately set to values other than the above to enhance sensitivity and specificity.

Figure 18C:
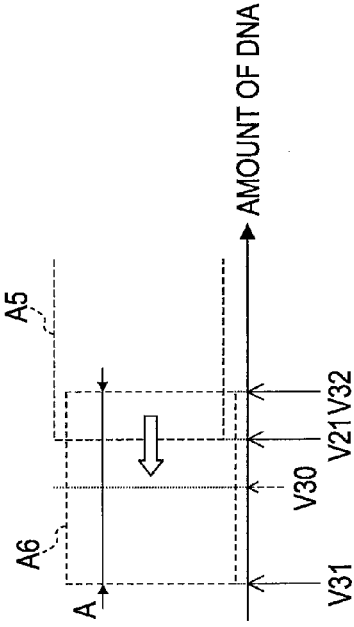
Figure 18D:
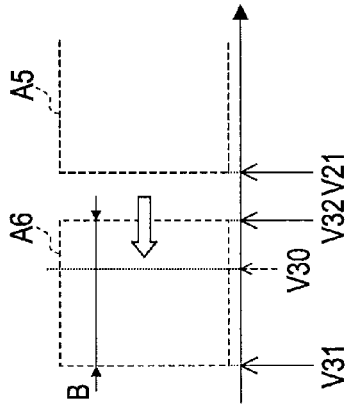

FIG. 18C is a view showing a state in which the range of the cell of 2C extracted in S111 of FIG. 9 is changed, that is, a state in which the right end of the region A6 of FIG. 10E is reduced. V31 and V32 of the region A6 of FIG. 18C include V30 in the range between V31 and V32, and the width of the range of V31 and V32 is set to be B, which is smaller than the width A of the range of V31 and V32 in FIG. 10E. FIG. 18D is a view showing a state in which the range of the cell of greater than or equal to the amount of DNA of the normal cell in the S period extracted in S107 of FIG. 9 is changed, that is, a state in which the left end of the region A5 of FIG. 10D is extended. The value V21 at the left end of the region A5 of FIG. 18D is set to be a value greater than V30 and smaller than V32 when V30 is included in the range between V31 and V32 and the width of the range of V31 and V32 is set to become A.

When the regions A5, A6 are set as in FIGS. 18C and 18D, and the determination on canceration is carried out for 1035 samples similar to the above, the sensitivity is 83.3%, similar to the embodiment described above, and the specificity is 98.7% and 98.5% in the determination 2, which is substantially the same as the embodiment described above. Therefore, determination can be appropriately made as "Cancer", similar to the embodiment described above, even if the range of cells to extract is changed.

In the embodiment described above, after S105 of FIG. 9, the cell group of V11≤N/C ratio≤V12 is first extracted, the cell group in which the amount of DNA is greater than or equal to the amount of DNA of the normal cell in the S period out of the extracted cell group is counted, and the counted value is used for the number of cells in S107 or the numerator of the canceration ratio in S111. Instead, however, the cell group in which the amount of DNA is greater than or equal to the amount of DNA of the normal cell in the S period may be extracted, the cell group of V11≤N/C ratio≤V12 out of the extracted cell group may be counted, and the counted value may be used for the number of cells in S107 or the numerator of the canceration ratio in S111.

In the embodiment described above, after S109 of FIG. 9, the cell group of V13≤N/C ratio≤V11 is first extracted, the cell group in which the amount of DNA is 2C out of the extracted cell group is counted, and the counted value is set as a denominator of the canceration ratio. Instead, however, the cell group in which the amount of DNA is 2C may be extracted, the cell group of V13≤N/C ratio≤V11 out of the extracted cell group may be counted, and the counted value may be set as the denominator of the canceration ratio in S111.

The embodiment of the present invention may be appropriately modified within a scope of a technical concept defined by the Claims.

What is claimed is:

1. A canceration information providing method for providing information related to canceration of cells, the method comprising:
   flowing, through a flow cell, a measurement specimen comprising epidermal cells of a uterine cervix;
   irradiating the measurement specimen flowing through the flow cell with light;
   detecting scattered light from each of the cells of the measurement specimen as a result of the irradiating the measurement specimen and generating a first signal representative of the scattered light;
   detecting fluorescence light from each of the cells of the measurement specimen as a result of the irradiating the measurement specimen and generating a second signal representative of the fluorescence light;
   acquiring for each of the cells of the measurement specimen first data related to a size of a cell nucleus of the cell from the second signal, second data related to a size of the cell from the first signal, and third data related to an amount of DNA of the cell from the second signal;
   based on the first data, the second data, and the third data, acquiring a number of first cells from the measurement specimen in which a ratio of the size of the cell nucleus with respect to the size of the cell is smaller than a predetermined threshold value and wherein the first cells have an amount of DNA of a normal cell in which a cell cycle is in a G0 period, defined to be a resting period in which a proliferation of a cell is resting, or a G1 period, defined to be timing of preparation and inspection from an end of the G0 period to a time to enter the DNA synthetic period of the cell;
   based on the first data, the second data, and the third data, acquiring a number of second cells from the measurement specimen in which the ratio of the size of the cell nucleus with respect to the size of the cell is within a predetermined range of greater than or equal to the threshold value and wherein the second cells have an amount of DNA exceeding the amount of DNA of the normal cell in which the cell cycle is in the G0 period or the G1 period;
   calculating a ratio of the acquired number of first cells and the number of second cells; and
   outputting information related to the canceration of the cells of the measurement specimen based on the calculated ratio, wherein the outputted information indicates at least one of whether a retest of the measurement specimen is necessary and whether cervical cancer is suspected for the measurement specimen.

2. The canceration information providing method according to claim 1, wherein the acquiring the number of first cells comprises:
   based on the first data and the second data, classifying the cells to be analyzed to a first cell group in which the ratio of the size of the cell nucleus with respect to the size of the cell is smaller than the predetermined threshold value; and
   based on the third data obtained from cells of the first cell group, acquiring the number of first cells having the amount of DNA of the normal cell in which the cell cycle is in the G0 period or the G1 period.

3. The canceration information providing method according to claim 1, wherein the acquiring the number of second cells further comprises:
based on the first data and the second data, classifying the cells to be analyzed to a second cell group in which the ratio of the size of the cell nucleus with respect to the size of the cell is within the predetermined range; and
based on the third data obtained from cells of the second cell group, acquiring the number of second cells having the amount of DNA exceeding the amount of DNA of the normal cell in which the cell cycle is in the G0 period or the G1 period.

4. The canceration information providing method according to claim 1, wherein the predetermined range is set with an upper limit and a lower limit.

5. The canceration information providing method according to claim 1, further comprising: determining a cell to be analyzed from a cell group contained in the measurement specimen.

6. The canceration information providing method according to claim 5, wherein the determining comprises: classifying the cell group contained in the measurement specimen to a cell of the same type as the cell to be analyzed and a cell of a different type from the cell to be analyzed.

7. The canceration information providing method according to claim 5, wherein the determining comprises:
classifying a cell of the same type as the cell to be analyzed as either an aggregated cell or a non-aggregated cell; and
determining the non-aggregated cell, when so classified, as the cell to be analyzed.

8. The canceration information providing method according to claim 5, wherein the outputting information related to the canceration of the cells occurs only when a number of cells to be analyzed which have been determined as a result of the determining process is greater than a predetermined number.

9. The canceration information providing method according to claim 1, wherein the second data is acquired based on a width of a waveform of the first signal.

10. A canceration information providing device for providing information relating to canceration of cells, the canceration information providing device comprising:
a flow cell configured to allow flow of a measurement specimen, comprising epidermal cells of a uterine cervix;
an optical source configured to allow irradiation with light the measurement specimen flowing through the flow cell;
a detector configured to 1) allow detection of scattered light from each of the cells of the measurement specimen irradiated by the optical source and allow generation of a first signal representative of the scattered light and 2) allow detection of fluorescence light from each of the cells of the measurement specimen irradiated by the optical source and allow generation of a second signal representative of the fluorescence light;
a controller having a structure to perform the operations comprising:
acquiring for each of the cells of the measurement specimen first data related to a size of a cell nucleus of the cell from the second signal, second data related to a size of the cell from the first signal, and third data related to an amount of DNA of the cell from the second signal;
acquiring a number of first cells from the measurement specimen in which a ratio of the size of the cell nucleus with respect to the size of the cell is smaller than a predetermined threshold value and wherein the first cells have an amount of DNA of a normal cell in which a cell cycle is in a G0 period, defined to be a resting period in which a proliferation of a cell is resting, or a G1 period, defined to be timing of preparation and inspection from an end of the G0 period to a time to enter the DNA synthetic period of the cell;
based on the first data, the second data, and the third data, acquiring a number of second cells from the measurement specimen in which the ratio of the size of the cell nucleus with respect to the size of the cell is within a predetermined range of greater than or equal to the threshold value and wherein the second cells have an amount of DNA exceeding the amount of DNA of the normal cell in which the cell cycle is in the G0 period or the G1 period;
calculating a ratio of the acquired number of first cells and the number of second cells; and
outputting information relating to the canceration of the cells based on the calculated ratio, wherein the outputted information indicates at least one of whether a retest of the measurement specimen is necessary and whether cervical cancer is suspected for the measurement specimen.

11. The canceration information providing device according to claim 10, wherein the detector comprises:
a scattered light detector configured to allow detection of the scattered light from each of the cells of the measurement specimen irradiated by the optical source; and
a fluorescence detector configured to allow detection of the fluorescence from each of the cells of the measurement specimen irradiated by the optical source.

12. The canceration information providing device according to claim 10, further comprising:
a display unit configured to allow display of the information relating to the canceration of the cells output by the controller.

13. The canceration information providing device according to claim 10, further comprising:
a specimen preparing unit comprising:
a container;
a pipette configured to transfer a biological specimen of the subject to the container; and
a dispenser configured to dispense a reagent to the container to prepare the measurement specimen.

* * * * *